(12) United States Patent
Morioka et al.

(10) Patent No.: US 6,611,728 B1
(45) Date of Patent: Aug. 26, 2003

(54) INSPECTION SYSTEM AND METHOD FOR MANUFACTURING ELECTRONIC DEVICES USING THE INSPECTION SYSTEM

(75) Inventors: Natsuyo Morioka, Tokyo (JP); Hisafumi Iwata, Hayama-machi (JP); Junko Konishi, Yokohama (JP); Yoko Ikeda, Yokohama (JP); Kazunori Nemoto, Akishima (JP); Makoto Ono, Yokohama (JP); Yasuhiro Yoshitake, Yokosuka (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/389,230

(22) Filed: Sep. 3, 1999

(30) Foreign Application Priority Data

Sep. 3, 1998 (JP) .............................. 10-249303
Sep. 3, 1998 (JP) .............................. 10-249935

(51) Int. Cl.[7] .............................................. G06F 19/00
(52) U.S. Cl. ........................ 700/109; 700/121; 700/175
(58) Field of Search ................................ 700/121, 109, 700/108, 175, 180, 192, 110, 111, 95, 96; 702/81, 84; 382/142

(56) References Cited

U.S. PATENT DOCUMENTS

| 4,347,001 A | * | 8/1982 | Levy et al. ................. 356/390 |
| 4,923,066 A | * | 5/1990 | Ophir et al. ................ 209/538 |
| 5,963,881 A | * | 10/1999 | Kahn et al. .................. 702/35 |
| 6,128,403 A | * | 10/2000 | Ozaki ........................ 382/145 |
| 6,292,582 B1 | * | 9/2001 | Lin et al. .................... 348/126 |
| 6,314,379 B1 | * | 11/2001 | Hu et al. ..................... 702/81 |
| 6,438,438 B1 | * | 8/2002 | Takagi et al. ............... 700/121 |

FOREIGN PATENT DOCUMENTS

WO   9628778   9/1996

OTHER PUBLICATIONS

Semiconductor World 1996.8, Process Technology for Devices, "Knights Technology Yield Manager".
Semiconductor World 1996.8, Process Technology for Devices, "AS–5000".
Hall et al., "Yield Monitoring and Analysis in Semiconductor Manufacturing".

* cited by examiner

Primary Examiner—Leo Picard
Assistant Examiner—Kidest Bahta
(74) Attorney, Agent, or Firm—Antonelli, Terry, Stout & Kraus, LLP

(57) ABSTRACT

An inspection system comprises an inspection machine for inspecting a work which is processed in one of the manufacturing processes of a manufacturing line and an analysis system for outputting an inspection history list obtained by making calculations from the inspected result. The inspection history list shows a matrix of first information as the inspection processes in which the work is inspected or the manufacturing processes corresponding to the inspection processes in which the work is inspected and second information as to the works inspected by the inspection machine.

17 Claims, 33 Drawing Sheets

FIG.5

| prod-uct name | lot num-ber | wafer num-ber | yield | num-ber of inspection | process name | inspection type | cluster | inspection date | image | process name | inspection type | cluster | inspection date | image | process name | inspection type | cluster | inspection date | image |
|---|---|---|---|---|---|---|---|---|---|---|---|---|---|---|---|---|---|---|---|
| Hin 1 | A01 | 10 | 55 | 22 | process 1 | 0 | 0 | 1999/3/3 7:05 | 0 | process 2 | 0 | 0 | 1999/3/5 7:34 | 0 | probe test | 2 | 0 | 1999/3/28 7:05 | 0 |
| Hin 1 | A01 | 20 | 58 | 22 | process 1 | 0 | 1 | 1999/3/3 7:20 | 0 | process 2 | 0 | 0 | 1999/3/5 7:54 | 0 | probe test | 2 | 0 | 1999/3/28 8:05 | 0 |
| Hin 1 | A02 | 5 | 67 | 21 | process 1 | 0 | 0 | 1999/3/5 8:27 | 1 | process 3 | 0 | 1 | 1999/3/9 2:27 | 1 | | | | | |
| Hin 1 | A02 | 15 | 65 | 21 | process 1 | 0 | 0 | 1999/3/5 8:48 | 0 | process 3 | 0 | 0 | 1999/3/9 2:30 | 0 | | | | | |
| Hin 1 | A02 | 25 | 54 | 21 | process 1 | 0 | 0 | 1999/3/5 9:02 | 0 | process 3 | 0 | 0 | 1999/3/9 2:45 | 0 | | | | | |
| Hin 1 | A03 | 3 | 58 | 18 | process 1 | 0 | 0 | 1999/3/8 3:00 | 0 | process 2 | 0 | 0 | 1999/3/10 8:03 | 0 | | | | | |
| Hin 1 | A03 | 13 | 60 | 18 | process 1 | 0 | 0 | 1999/3/8 3:24 | 0 | process 2 | 0 | 0 | 1999/3/10 8:29 | 0 | | | | | |
| Hin 1 | A03 | 23 | 52 | 18 | process 1 | 0 | 0 | 1999/3/8 3:49 | 0 | process 2 | 0 | 0 | 1999/3/10 8:49 | 0 | | | | | |
| Hin 1 | A04 | 1 | 34 | 22 | process 1 | 0 | 1 | 1999/3/10 5:49 | 0 | process 2 | 0 | 1 | 1999/3/12 5:49 | 0 | probe test | 2 | 0 | 1999/4/10 4:07 | 0 |
| Hin 1 | A04 | 20 | 34 | 22 | process 1 | 0 | 0 | 1999/3/10 6:09 | 1 | process 2 | 0 | 0 | 1999/3/12 6:09 | 1 | probe test | 2 | 0 | 1999/4/10 5:07 | 0 |
| Hin 1 | k01 | 5 | | 6 | process 2 | 0 | 1 | 1999/7/2 2:25 | 1 | process 3 | 0 | 0 | 1999/7/3 7:05 | 0 | | | | | |
| Hin 1 | k01 | 15 | | 8 | process 2 | 0 | 0 | 1999/7/2 2:45 | 0 | process 3 | 0 | 1 | 1999/7/3 7:20 | 0 | | | | | |
| Hin 1 | k02 | 5 | | 5 | process 1 | 0 | 0 | 1999/7/3 7:05 | 0 | process 3 | 0 | 0 | 1999/7/5 6:27 | 1 | | | | | |
| Hin 1 | k02 | 15 | | 5 | process 1 | 0 | 0 | 1999/7/3 7:25 | 1 | process 3 | 0 | 0 | 1999/7/5 6:48 | 0 | | | | | |
| Hin 1 | k02 | 25 | | 5 | process 1 | 0 | 0 | 1999/7/3 7:45 | 0 | process 3 | 0 | 0 | 1999/7/6 9:02 | 0 | | | | | |
| Hin 1 | k03 | 3 | | 3 | process 1 | 0 | 0 | 1999/7/5 3:09 | 0 | process 3 | 0 | 0 | 1999/7/6 3:09 | 0 | | | | | |
| Hin 1 | k03 | 13 | | 3 | process 1 | 0 | 0 | 1999/7/5 3:29 | 0 | process 3 | 0 | 0 | 1999/7/8 3:29 | 0 | | | | | |
| Hin 1 | k03 | 23 | | 3 | process 1 | 0 | 0 | 1999/7/5 3:49 | 1 | process 3 | 0 | 0 | 1999/7/8 3:49 | 1 | | | | | |
| Hin 1 | k04 | 1 | | 1 | process 1 | 0 | 1 | 1999/7/6 13:18 | 0 | process 4 | 0 | 1 | 1999/7/10 5:49 | 0 | | | | | |
| Hin 1 | k04 | 20 | | 1 | process 1 | 0 | 0 | 1999/7/6 13:36 | 0 | process 4 | 0 | 0 | 1999/7/10 6:09 | 1 | | | | | |

FIG.9 product name (901): Hin 1
lot number (902): NO1
wafer number (903): 5
transaction parameter of making DLH list (904): 256 256 1 8 10 250
inspection date (909):
- process 1  1999/07/27 03:35:07
- process 2  1999/07/29 05:26:31
- process 3  1999/07/31 07:23:45 inspected process name (905)

| defect coordinates (906) | | defect count in each process (907) | | | defect generated process (908) | | | size (913) | defect category (910) | cluster (911) | image index (912) | | |
|---|---|---|---|---|---|---|---|---|---|---|---|---|---|
| 23115.70 | 45894.32 | 1 | 0 | 0 | 0 | 255 | 0 | 1 | 1 | 1 | 0 | 0 | 0 |
| 50585.37 | -17273.83 | 1 | 0 | 1 | 0 | 255 | 255 | 0 | 2 | 0 | 0 | 0 | 0 |
| 10361.40 | 69454.50 | 1 | 0 | 0 | 0 | 255 | 255 | 0 | 2 | 3 | 0 | 0 | 0 |
| 10778.87 | 6274.35 | 1 | 0 | 2 | 0 | 255 | 0 | 1 | 1 | 4 | 0 | 7 | 0 |
| -18731.05 | 20437.45 | 1 | 1 | 0 | 0 | 0 | 255 | 2 | 0 | 5 | 0 | 0 | 0 |
| -18781.02 | 20487.29 | 1 | 0 | 0 | 0 | 255 | 255 | 3 | 0 | 5 | 0 | 0 | 0 |
| -18688.05 | 20387.45 | 1 | 1 | 0 | 0 | 0 | 255 | 0 | 0 | 5 | 0 | 0 | 0 |
| -10711.01 | -10775.37 | 1 | 0 | 2 | 0 | 255 | 0 | 1 | 1 | 6 | 0 | 0 | 0 |
| 30100.95 | -17243.44 | 1 | 1 | 0 | 0 | 0 | 255 | 2 | 0 | 7 | 0 | 4 | 0 |
| -31423.83 | -24935.72 | 1 | 0 | 0 | 0 | 255 | 255 | 3 | 0 | 8 | 0 | 0 | 0 |
| -917.65 | -2617.23 | 0 | 1 | 0 | 255 | 0 | 255 | 0 | 0 | 9 | 0 | 0 | 0 |
| 9437.81 | -38263.98 | 0 | 1 | 0 | 255 | 0 | 255 | 0 | 0 | 0 | 0 | 0 | 0 |
| 9500.81 | -38220.67 | 0 | 1 | 0 | 255 | 0 | 255 | 0 | 0 | 0 | 0 | 0 | 0 |
| 26867.07 | -95572.77 | 0 | 0 | 1 | 255 | 255 | 0 | 3 | 0 | 0 | 1 | 3 | 0 |
| -35343.07 | 14424.21 | 0 | 0 | 1 | 255 | 255 | 0 | 0 | 2 | 0 | 0 | 0 | 0 |
| -27068.01 | -7597.72 | 0 | 1 | 1 | 255 | 0 | 0 | 2 | 2 | 0 | 1 | 0 | 0 |
| 6938.41 | 941.94 | 0 | 0 | 1 | 255 | 255 | 0 | 0 | 3 | 0 | 0 | 0 | 0 |
| -5153.42 | -1570.01 | 0 | 0 | 1 | 255 | 255 | 0 | 0 | 4 | 0 | 0 | 0 | 0 |
| -71387.54 | -2417.33 | 0 | 0 | 1 | 255 | 255 | 0 | 2 | 5 | 0 | 0 | 0 | 0 |
| -9262.01 | 1549.27 | 0 | 0 | 1 | 255 | 255 | 0 | 2 | 0 | 0 | 0 | 0 | 0 |
| | | 0 | 0 | 0 | 255 | 255 | 255 | 1 | 0 | 0 | 0 | 0 | 0 |
| | | 0 | 0 | 0 | 255 | 255 | 255 | 0 | 0 | 0 | 0 | 0 | 0 |
| | | 0 | 0 | 0 | 255 | 255 | 255 | 0 | 0 | 0 | 0 | 0 | 0 |
| | | 0 | 0 | 0 | 255 | 255 | 255 | 2 | 0 | 0 | 0 | 0 | 0 |
| | | 0 | 0 | 0 | 255 | 255 | 255 | 2 | 0 | 0 | 0 | 0 | 0 |
| | | 0 | 0 | 0 | 255 | 255 | 255 | 2 | 0 | 0 | 0 | 0 | 0 |
| | | 0 | 0 | 0 | 255 | 255 | 255 | 2 | 0 | 0 | 0 | 0 | 0 |
| | | 0 | 0 | 0 | 255 | 255 | 255 | 2 | 0 | 5 | 0 | 0 | 0 |
| | | 0 | 0 | 0 | 255 | 255 | 255 | 2 | 0 | 1 | 0 | 0 | 0 |
| | | 0 | 0 | 0 | 255 | 255 | 255 | 2 | 0 | 2 | 0 | 0 | 0 |
| | | 0 | 0 | 0 | 255 | 255 | 255 | 1 | 0 | 3 | 0 | 0 | 0 |
| | | 0 | 0 | 0 | 255 | 255 | 255 | 2 | 0 | 4 | 0 | 0 | 0 |

FIG.10

| lot number | wafer number | process 1 | process 2 | process 3 | process 4 | process 5 | process 6 | process 7 |
|---|---|---|---|---|---|---|---|---|
| NO1 | 5 | ○ | ○ | ○ | ○ | ○ | ○ | ○ | defect map gallery

```
<product name>    Hin1
<lot number>      NO1
<wafer number>    5
<process name>    process 1
<date>            1999/07/27  03:35:07
<defect coordinates>
   1,     23115.70,      45894.32,  S,
   2,     50585.37,     -17273.83,  S,
   3,     10361.40,      69454.50,  M,
   4,     10778.87,       6274.35,  L,
   5,    -18731.05,      20437.45,  L,
   6,    -18781.02,      20487.29,  M,
   7,    -18688.05,      20387.45,  L,
   8,    -10711.01,     -10775.37,  S,
   9,     30100.95,     -17243.44,  M,
  10,    -31423.83,     -24935.72,  L,
```

<product name>    Hin1
<lot number>      NO1
<wafer number>    5
<process name>    process 1
<date>            1999/08/18  05:55:41
<location>        10778.87, 6274.35
<image>

FIG.27

⟨product name⟩ Hin1
⟨lot number⟩ NO1
⟨wafer number⟩ 5
⟨result⟩
    2, 5,   A
    3, 5,   B
    4, 5,   B
    5, 5,   C
    1, 4,   A
    2, 4,   A
    3, 4,   C
    4, 4,   B
    5, 4,   G
    6, 4,   G
    1, 3,   K
    2, 3,   J
    3, 3,   J
    4, 3,   /
    5, 3,   H
    6, 3,   M
    1, 2,   A
    2, 2,   A
    3, 2,   C
    4, 2,   B
    5, 2,   B
    6, 2,   D
    2, 1,   C
    3, 1,   C
    4, 1,   C
    5, 1,   C

FIG.29

Hin1 `product name` ~2901
NO1 `lot number` ~2902
5 `wafer number` ~2903
256 256 1 8 10 250 `transaction parameter of making DLH list` ~2904
process 1
process 2
process 3

2905 `inspected process name`

| | defect coordinates 2906 | | defect count in each process 2907 | | | defect generated process 2908 | | | size 2909 | | | defect category 2910 | | | cluster 2911 | | | image index 2912 | | |
|---|---|---|---|---|---|---|---|---|---|---|---|---|---|---|---|---|---|---|---|---|
| (1)  | 23115.70  | 45894.32   | 1 | 0 | 1 | 0   | 0   | 0   | 1 | 0 | 2 | 1 | 0 | 1 | 0 | 0 | 0 | 0 | 0 | 0 |
| (2)  | 50585.37  | -17273.83  | 1 | 0 | 0 | 0   | 255 | 255 | 1 | 0 | 0 | 2 | 0 | 0 | 0 | 0 | 0 | 0 | 0 | 0 |
| (3)  | 10361.40  | 69454.50   | 1 | 1 | 0 | 0   | 255 | 255 | 2 | 0 | 0 | 3 | 0 | 0 | 0 | 0 | 0 | 0 | 0 | 0 |
| (4)  | 10778.87  | 6274.35    | 1 | 1 | 2 | 0   | 0   | 0   | 3 | 1 | 2 | 4 | 4 | 4 | 0 | 0 | 0 | 1 | 4 | 7 |
| (5)  | -18731.05 | 20437.45   | 1 | 1 | 0 | 0   | 255 | 255 | 3 | 1 | 0 | 5 | 5 | 0 | 1 | 0 | 0 | 2 | 0 | 0 |
| (6)  | -18781.02 | 20487.29   | 1 | 1 | 0 | 0   | 0   | 255 | 2 | 0 | 0 | 5 | 0 | 0 | 1 | 0 | 0 | 0 | 0 | 0 |
| (7)  | -18688.05 | 20387.45   | 1 | 1 | 2 | 0   | 255 | 0   | 3 | 2 | 0 | 5 | 5 | 0 | 1 | 0 | 0 | 0 | 0 | 0 |
| (8)  | -10711.01 | -10775.37  | 1 | 1 | 0 | 0   | 0   | 255 | 1 | 2 | 3 | 7 | 7 | 0 | 0 | 0 | 0 | 0 | 0 | 0 |
| (9)  | 30100.95  | -17243.44  | 1 | 0 | 0 | 0   | 255 | 255 | 2 | 0 | 0 | 8 | 0 | 0 | 0 | 0 | 0 | 0 | 0 | 8 |
| (10) | -31423.83 | -24935.72  | 1 | 0 | 0 | 0   | 255 | 255 | 3 | 0 | 0 | 9 | 0 | 0 | 0 | 0 | 0 | 3 | 0 | 0 |
| (11) | -917.65   | -2617.23   | 0 | 1 | 0 | 255 | 1   | 1   | 0 | 1 | 0 | 0 | 1 | 0 | 0 | 0 | 0 | 0 | 0 | 0 |
| (12) | 9437.81   | -38263.98  | 0 | 1 | 0 | 255 | 1   | 1   | 0 | 3 | 0 | 0 | 2 | 0 | 0 | 1 | 0 | 0 | 5 | 0 |
| (13) | 9500.81   | -38220.67  | 0 | 1 | 0 | 255 | 1   | 1   | 0 | 2 | 0 | 0 | 2 | 0 | 0 | 1 | 0 | 0 | 0 | 0 |
| (14) | 26867.07  | -95572.77  | 0 | 1 | 0 | 255 | 1   | 255 | 0 | 3 | 0 | 0 | 3 | 0 | 0 | 0 | 0 | 0 | 6 | 0 |
| (15) | -35343.07 | 14424.21   | 0 | 1 | 1 | 255 | 1   | 1   | 0 | 1 | 0 | 0 | 4 | 0 | 0 | 1 | 0 | 0 | 0 | 0 |
| (16) | -27068.01 | -7597.72   | 0 | 0 | 1 | 255 | 255 | 1   | 0 | 2 | 2 | 0 | 5 | 5 | 0 | 0 | 0 | 0 | 0 | 0 |
| (17) | 6938.41   | 941.94     | 0 | 0 | 1 | 255 | 255 | 2   | 0 | 0 | 2 | 0 | 0 | 1 | 0 | 0 | 0 | 0 | 0 | 9 |
| (18) | -5153.42  | -1570.01   | 0 | 0 | 1 | 255 | 255 | 2   | 0 | 0 | 1 | 0 | 0 | 2 | 0 | 0 | 0 | 0 | 0 | 0 |
| (19) | -71387.54 | -2417.33   | 0 | 0 | 1 | 255 | 255 | 2   | 0 | 0 | 2 | 0 | 0 | 3 | 0 | 0 | 0 | 0 | 0 | 0 |
| (20) | -9262.01  | 1549.27    | 0 | 0 | 1 | 255 | 255 | 2   | 0 | 0 | 1 | 0 | 0 | 4 | 0 | 0 | 0 | 0 | 0 | 0 |

INSPECTION SYSTEM AND METHOD FOR MANUFACTURING ELECTRONIC DEVICES USING THE INSPECTION SYSTEM

BACKGROUND OF THE INVENTION

The present invention relates to an inspection system applied to a production line of electronic devices, etc., and a method for manufacturing electronic devices using such an inspection system.

More particularly, the present invention relates to an inspection system for inspecting electronic devices, which is enhanced for effective obtainment of inspection data and improvement of data analysis speed by making it easy to select and extract wafers to be inspected and analyzed, and for a method for manufacturing electronic devices, etc. using such an inspection system.

Electronic devices such as semiconductor devices are formed through repetitive treatments of wafers, which includes a plurality of processes such as photolithography, etching, etc. On the other hand, wafers treated in a predetermined process among a plurality of such manufacturing processes are inspected as needed by a particle inspection machine, a visual inspection machine, etc., and then particle information and improper shape information as to positions, sizes, quantities, types, etc. are collected. Hereafter, particle information to be detected by a particle inspection machine and improper shape information to be detected by a visual inspection machine will both be referred to as defect information generically.

As described in a monthly publication "Semiconductor World" (August, 1996, pp. 88, 99 and 102), inspection results have been transmitted from an inspection machine to an analysis unit through a network. And, the analysis unit can output any kind of analysis picture as needed, such as a trend of the total number of defects, a vertical bar graph (stack chart) for displaying the detected defect count in each defect-detected process, and/or a chart of correlation between defect count and yield, wherein the yield is calculated by using inspection results of electrical characteristics.

By using such analysis pictures, analyzers have checked and analyzed whether or not the defect count exceeds a predetermined standard, whether or not there is any abnormal defect-detected process, and whether or not there is any unique distribution of defects, and have tracked a source of various problems by using the analysis result. After that, analyzers have identified a defect-detected process and/or manufacturing equipment. Then they have tried to improve these processes and/or the manufacturing equipment to ramp up yield.

Conventionally, an object wafer, lot, or section between processes to analyze has been identified just subjectively by such analyzers, and then the identified object has been analyzed as described above.

BRIEF SUMMARY OF THE INVENTION

If desired, electrical characteristics (e.g., product functional tests) of electronic devices such as semiconductor devices can be inspected for all of the wafers in a production line (100%) being processed. However, practically, defect inspections inspected by particle inspection machines or visual inspection machines are not performed on all of the wafers and are not performed in every process in order to keep the through-put of a production line up to a predetermined level.

Generally, these defect inspections are performed on some desired wafers which are processed in a desired process. Consequently, if analyzers select desired wafers and/or processes just on the basis of their subjectivity for making the above-discussed analysis pictures, they are likely to select wrong wafers that are not inspected in the desired process. If analyzers select these wrong wafers, the above-discussed analysis pictures such as trend charts and stack charts for the total number of defects cannot be calculated. Furthermore, if a selected wafer has many peculiar defects such as a cluster which is mainly caused by bad condition of the manufacturing equipment, an analysis result on the basis on these peculiar defects cannot be accepted as an analysis result of the real average capability of the manufacturing line.

For example, when yield loss impacts caused by defects are analyzed, a correlation between the defects generated in each process and the pass/fail(electrical characteristics) state of each chip on a completed wafer must be taken. In this case, the object wafers are required to be inspected in many processes, to not have any cluster data which causes analytical errors and to have a comparatively high yield to establish a correlation with defects and yield.

And furthermore, it will be very effective to make a comparison between detailed electrical characteristics (e.g., a memory fail bit map data) and a defect inspection result in order to identify a process which causes failure chips. Since this inspection process of detailed electrical characteristics is performed after an object wafer is finished, in this case, one needs to identify which wafers have been inspected consistently in the manufacturing processes.

In the case of the conventional analyzing system, however, an object wafer to be analyzed has been selected only by the subjectivity of the analyzer. Consequently, an analyzer needs to repeat selection of wafers many times until the suitable one is selected. For example, this selection might have to be repeated until a wafer that has no dense defects (cluster) appears. For that reason, the conventional analyzing system needs to spend a longer analyzing time, thereby delaying feedback of the analysis result to the manufacturing process. In addition, it is not certain whether or not the selected wafer is really a suitable one for the analysis.

In addition, even when a specific defect position is selected from data obtained in an analysis unit and observed to capture its image, it is not easy to retrieve past detected information of the wafer. It has thus been impossible to select newly found defects or defects for which images were already captured in previous processes.

When wafers are enlarged in diameter, for example, to 300φ, the amount of data to be treated in the inspection process will be increased. As a result, the preparation time for analysis/inspection time will further increase.

Under such circumstances, it is an object of the present invention to make it easier to select an object wafer to be analyzed or inspected, thereby shortening the analyzing time or time for obtaining inspection data effectively.

In addition, in many conventional analyzing systems, such inspection data are retrieved and computed from a database when a user analyzes the inspection data. Some conventional analyzing systems can compute such inspection data before receiving an instruction from a user, however such systems can compute only respective analytic operations independently. Consequently, if an analysis is to be made by freely combining all the information items related to defects on a wafer, a processing time must be taken into account for each of searching and computing operations separately. As a result, a long preparation time is needed for each of such searching and computing operations. This is why it usually takes much time to feed back analyzed data to an object manufacturing process.

Under such circumstances, it is an object of the present invention to provide a system for inspecting electronic devices and a method for manufacturing electronic devices using such a system, which are enhanced for reduction of analyzing time and improvement of analyzing accuracy by solving the conventional problems and making it easier to use a large amount of defect inspection data thereby to shorten the preparing time for analysis.

In order to achieve the above object, an inspection system is provided which includes an inspection machine for inspecting a work which is processed in one of a plurality of manufacturing processes of a manufacturing line and an analysis system for outputting an inspection history list obtained by making calculations from the inspected result. The inspection history list shows a matrix of first information as to the inspection processes in which the work is inspected or the manufacturing processes corresponding to the inspection processes in which the work is inspected and second information as to the works inspected by the inspected machine.

The above inspection history list shows whether or not characteristic defects are included in the inspection result of the inspection process in which the work is inspected or the manufacturing process corresponding to the inspection process in which the work is inspected. One such characteristic defect is cluster.

The above inspection system can further include a test machine for testing the electrical characteristic of the work, wherein the inspection history list shows whether or not the electrical characteristic of the work is included.

The above inspection system can further include a plurality of the inspection machines, wherein the inspection machines can be visual inspection machines and/or particle inspection machines.

The above inspection system can further include an observation machine for capturing a defect image of the work, wherein the inspection history list shows whether or not the defect image of the work is included in the inspection result of the inspection process in which the work is inspected or the manufacturing process corresponding to the inspection process in which the work is inspected.

The above analysis system can comprise client-server system.

The above first information can further include data regarding the inspection processes in which a work is not being inspected or the manufacturing processes corresponding to the inspection processes in which a work is not being inspected.

In addition, an inspection system is provided comprising an inspection machine for inspecting a work which is processed in one of the manufacturing processes of a manufacturing line and an analysis system for creating a defect location history list for each piece of work according to inspection results obtained by the inspection machine before receiving an analysis instruction.

The above analysis system creates a defect location history list for each piece of work according to inspection results obtained by the inspection machine before receiving an analysis instruction.

The above analysis system creates the inspection history list by using the defect location history list.

In addition, an inspection system comprising an inspection machine for inspecting a work which is processed in one of the manufacturing processes of a manufacturing line and an analysis system for displaying a matrix of first information as to the inspection processes in which the work is inspected or the manufacturing processes corresponding to the inspection processes in which the work is inspected and second information as to the works inspected by the inspected machine.

In addition, an inspection system comprising an inspection machine for inspecting a work which is processed in one of the manufacturing processes of a manufacturing line and an analysis system for displaying both inspection processes in which the work is inspected and inspection processes in which the work is not inspected or both the manufacturing processes corresponding to the inspection processes in which the work is inspected and the manufacturing processes corresponding to the inspection processes in which the work is not inspected.

In addition, an analysis system comprising a storing means for storing inspection results and an outputting means for outputting an inspection history list calculated by using said stored inspection results, said inspection history list showing a matrix of first information as to the inspection processes in which the work is inspected or the manufacturing processes corresponding to the inspection processes in which the work is inspected and second information as to the works inspected by the inspected machine.

The above first information further includes the inspection processes in which a work is not inspected or the manufacturing processes corresponding to the inspection processes in which a work is not inspected.

In addition, a method for producing electrical devices comprising a processing step for processing works in a manufacturing line, an inspecting step for inspecting a work which is processed in one of the manufacturing processes of the manufacturing line by an inspection machine, an analyzing step for analyzing defects information obtained by making calculations from the inspected result, said defects information showing a matrix of the first information as to inspection processes in which the work is inspected or the manufacturing processes corresponding to the inspection processes in which the work is inspected and second information as to a plurality of the works inspected by the inspected machine and a controlling step for controlling the manufacture line on the basis of the result of the analysis.

The above defects information shows whether or not characteristic defects are included in the inspection result of the inspection process in which the work is inspected or the manufacturing process corresponding to the inspection process in which the work is inspected, said analyzing step for analyzing defects information without the characteristic defects. As an example, the above-mentioned characteristic defect can be cluster.

According to the present invention, the wafer inspection state is over viewed completely by using the inspection history list, thereby to select desired wafers to be analyzed easily. The conventional analyzers have not been able to provide such an overview. In other words, by overviewing how the wafers have been inspected so far, this make it easy to select a proper target wafer to be analyzed, thereby shortening the analyzing time and obtaining the inspection data effectively.

Furthermore, since the inspection system of the present invention is composed to be able to analyze only specific inspection results including peculiar items such as cluster and only ordinary inspection results not including peculiar items, it is possible to analyze with proper inspection result according to purpose of that analysis, thereby to improve the analyzing accuracy.

Furthermore, for example, since it is possible to select inspection processes to be excluded from an analysis object by using an inspection history list, it is easy to select the same inspection processes among the objected wafers (i.e., the wafers selected for inspection), thereby to make the conditions of counting the number of defects (added defects) detected in each inspection process even and improving the analyzing accuracy, and accordingly providing highly reliable analysis results.

Furthermore, since it is possible to select proper wafers having no cluster through all of the inspection processes and display a vertical bar graph (stack chart) as divided for each defective appearing process, which shows an average value of the generated defect counts in the processes, it is also possible to analyze the inspection results without cluster, thereby analyzing abnormalities caused by process conditions more accurately. Such clusters are mainly caused by the manufacturing equipment condition.

And, since it is possible to select proper wafers having no cluster through all of the inspection processes and display a trend of the number of added defects detected in a target process within a specified period, it is possible to analyze the inspection results without cluster, thereby detecting abnormalities caused by process conditions more accurately.

In addition, in order to achieve the above object, the analysis system of this invention can include an analysis unit for creating first information according to inspection results obtained by a plurality of inspection machines before receiving analysis instruction and for creating second information according to the first information after receiving the analysis instruction, said second information showing the inspection processes in which a work is inspected or the manufacturing process corresponding to the inspection process in which the work is inspected.

In addition, the analysis system of this invention can include a storing means for storing inspection results and an outputting means for outputting an inspection history list calculated by using said stored inspection results, said inspection history list showing first information as to the inspection processes in which a work is inspected or the manufacturing processes corresponding to the inspection processes in which a work is inspected.

In this way, the present invention enables inspection result data stored in an analysis unit for each wafer as a defect location history list. It consists of coordinates of each defect, its attribute, cluster information and captured image indexes so that all the past information items of each of the defects on a wafer can be referenced in one defect location history list. The cluster information is a result of determination of a density of defect coordinates. The attribute can include items such as quantity, size, and type of each defect detected on a wafer.

Consequently, the present invention can prearrange searching and computing operations for data analysis, so that the preparing time for analysis is reduced significantly.

The present invention has also enabled each defect location history list to be transmitted to inspection machines connected through a network.

It is thus possible now to delete all of the past defect data detected on a wafer from the current inspection data in inspection machines, so that only newly detected defects can be inspected. For example, the number of new defects generated in a manufacturing process can be known on the very inspection site, so that abnormalities detected in a manufacturing process can be fed back speedily to the manufacturing process.

In the same way, the above defect location history list can be transmitted to a defect observing unit connected through a network.

This has made it possible to observe defects to be grown through manufacturing processes, as well as defects newly generated in a manufacturing process. It is thus possible now to observe and capture defect images more effectively, since the causes of those defects are cleared.

More concretely, the system of the present invention includes a plurality of processes for treating pieces of work and a plurality of inspection machines for inspecting each piece of work treated in the processes. The system of the present invention is connected to those inspection machines via a network and further includes an analysis unit provided with at least storing means for storing inspection results obtained from the inspection machines. The system of the present invention classifies inspection data stored in the analysis unit according to the coordinates of each defect. Inspection data in a process is then processed by a cluster identifying process and a process identifying process. A cluster identifying process means a determination of the density of the defects. On the other hand, in the process identifying process, the coordinates of each detected defect are also compared with the coordinates of the defects detected in the past so as to identify each process in which each object defect is detected. After this, the processing result, the inspection process name and the defect size attached to each defect are added to the defect location history list. Consequently, the defect location history list created for each wafer is expanded in size as it goes through the manufacturing processes.

The present invention also enables a defect location history list created by the analysis terminal unit beforehand to transmit to a data analysis terminal, an inspection machine, or a defect observing machine as defect historical information of each wafer.

BRIEF DESCRIPTION OF THE DRAWINGS

FIG. 5 is a configuration of an inspection history list indicating an example of the present invention.

FIG. 9 is a configuration of a defect location history list indicating an example of the present invention.

FIG. 10 shows the functions of an analyzing system using a defect location history list indicating an example of the present invention.

FIG. 27 is a configuration of electrical testing data indicating an example of the present invention.

FIG. 29 is a block diagram indicating a concrete example of the defect location history list shown in FIG. 28.

DESCRIPTION OF THE PREFERRED EMBODIMENT

Examples of the present invention will be described in detail with reference to the accompanying drawings.

Figure 1:
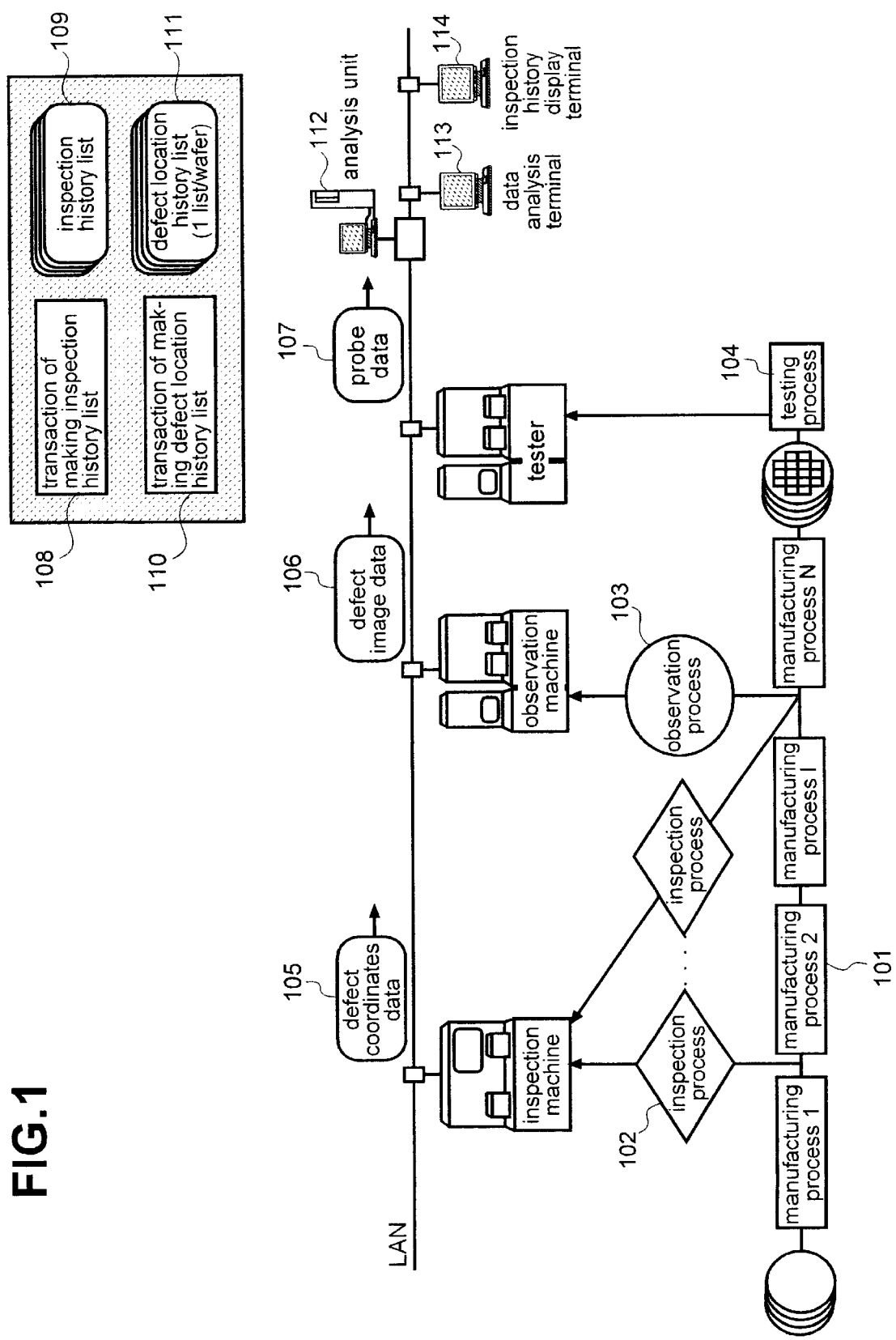
FIG. 1 is a block diagram of an inspection system indicating an example of the present invention.

FIG. 1 is a block diagram of an inspection system of the present invention as a whole.

In FIG. 1, numeral 101 indicates manufacturing processes for manufacturing electronic devices such as wafers of a semiconductor. 102 is an inspection process for inspecting unfinished wafers, such as particle inspection, visual inspection, etc. . 103 is an observation process for observing defects detected in the inspection process and capturing an image of those defects. 104 is a testing process for determining pass/fail among finished wafers. Each inspection process 102 outputs defect coordinates data 105, which is a result of a wafer inspection. The observation process 103 outputs defect image data 106. The testing process 104 outputs probe data 107.

The analysis unit 112 has defect coordinate data 105, defect image data 106, and probe data 107 thereby to create an inspection history list 109 through a transaction 108 of making the inspection history list and creating a defect location history list 111 through a transaction 110 of making the defect location history list.

An inspection history list 109 lists information showing executed inspection states of each wafer. The list 109 includes items of wafer ID, inspection process name, inspection time/date, and inspection type, as well as inspection specific items such as presence/absence of dense defects (cluster), presence/absence of a captured defect image, and yield.

A defect location history list 111 lists information showing detected defect states of each wafer. The list 111 includes defect coordinates and attributions such as items of defect detected processes, the number of defects existing in the proximity of the defect coordinates, defect size, defect category, cluster information, which is a result of a determination of defect density, and captured defect image index information. The inspection history list 109 and the defect location history list 111 will be described in more detail later.

The data analysis terminal 113 obtains an inspection history list 109 from the analysis unit 112 according to, for example, the object wafer ID. Then, the data analysis terminal 113 obtains a defect location history list 111 according to the information of an object wafer decided by referencing to the inspection history list 109, for example, the product name/lot number/wafer number. Then, the data analysis terminal 113 computes for a desired analysis operation by using the defect location history list 111 and displays the result.

The inspection history display terminal 114 obtains an inspection history list 109 from the analysis unit 112 according to, for example, the product name information of the object wafer, then references to the list 109 thereby to display the inspection history list.

The inspection machine used in the inspection process 102, the observation machine used in the observation process 103, the tester used in the testing process 104, the analysis unit 112, the data analysis terminal 113, and the inspection history display terminal 114 are connected to each other through a network.

Next, the operation of the inspection system shown in FIG. 1 will be described.

At first, in the manufacturing processes 101, each of the wafers receives a plurality of treatments such as deposition, photolithography, etching, etc. to form desired electric circuits thereon.

Figures 25, 26:
FIG. 25 is a configuration of defect inspection result data indicating an example of the present invention.
FIG. 26 is a configuration of observation result data indicating an example of the present invention.

On the other hand, wafers, treated in the one of the manufacturing process 101, are transferred to an inspection process 102. Then, these wafers are inspected for defects such as particles stuck thereon or improper shapes by using a particle inspection machine or a visual inspection machine. FIG. 25 shows an example of results of defect inspection, which are inspected for defects by using a particle inspection machine or a visual inspection machine. The inspection result includes information for identifying an object wafer such as product name, lot number, wafer number, and process name in which the object wafer was treated before the inspection, and information as to defect coordinates of the object wafer. In addition, as shown in FIG. 25, the inspection result may also include inspection time and the defect size. The inspection result further includes information for distinguishing inspection results between particle inspection results and visual inspection results, which is not shown in FIG. 25.

Furthermore, some wafers are transferred to the observation process 103 as needed so as to capture defect images thereof using an observation machine such as a review station, an SEM, etc. FIG. 26 shows an example of such an observation result obtained through an observation performed by an observation machine. The observation result includes information for identifying an object wafer such as product name, lot number, wafer number, etc., information as to processes in which the object wafer has been treated before observation, and image information which is an observation result. In addition, as shown in FIG. 26, the observation result may also include the observing time/date and the defect coordinates on the wafer.

After finishing all the treatments in the manufacturing processes 101, the finished wafers are transferred to the testing process 104, where each electric device(chip) formed on the wafer is checked pass or fail using a tester. FIG. 27 shows an example of probe data obtained through the testing process performed by a tester. These data are electrical characteristics of the chips. The probe data includes information for identifying an object wafer such as product name, lot number, wafer number, each object chip position information on the wafer, and each inspected chip result(pass/fail).

The inspection results and the observation results shown in FIG. 25 through FIG. 27 are transmitted to the analysis unit 112 from the defect inspection machine, the observation machine, and the tester each time when an inspection or observation is ended or periodically at a predetermined time.

Receiving these inspection and observation results, the analysis unit 112 generates an inspection history list 109 as shown in FIG. 5 according to identification information such as product name, lot number and wafer number. In other words, the analysis unit 112 generates data including the identification information items (501 to 503) such as product name, lot number, wafer number, etc., and the items of defect inspected process name 505, presence/absence state of an image (observation result)509 captured in the process, and presence/absence state of probe test 511. In FIG. 5, the analysis unit 112 also generates other information such as items of yield 510, the number of inspections 504 indicating how many times an object wafer has been inspected, inspection type information 506 for distinguishing between particle inspection and visual inspection, cluster information 507 indicating whether or not dense defects (cluster) are included in an object defect inspection result, and inspection time 508 indicating when an object defect inspection was made. However, these information items may be composed corresponding to the purpose of analysis. For example, in case of displaying only processes in which a defect inspection was performed, it is enough to generate the process name 505 for each of the identification information items (501 to 503) such as product name, lot number, wafer number, etc.

As described above, an inspection history list 109 is a list showing how the object wafer has been inspected and these inspection results. For example, an inspection history list 109 has process name, inspection time, inspection type, and inspection specific items (e.g., presence/absence of cluster and presence/absence of captured images) according to each inspection. If necessary, a value of specific electrical characteristics may also be added as a specific item of FIG. 5.

Receiving defect coordinates data 105, the analysis unit 112 counts up the item "number of inspections" 504 and describes the process name 505, the inspection type 506, the inspection date 508, and the cluster presence/absence information 507 in the inspection history list 109 on the basis of the inspection result shown in FIG. 25. In the case of the cluster presence/absence information 508, for example, if a cluster exists, 1 as the flag is set and if no cluster exists, 0 as the flag is set. As for the inspection type 506, for example, 0 is set for describing a particle inspection machine and 1 is set for describing a defect inspection. Since defect inspection data does not include image information, a no-image flag is set. For example, 0 is described as a no-image flag. And, if defect coordinates data 105 was received at the analysis unit 112 , the number of inspections 504 is incremented by one and the inspection progress and the result are described in the list.

In this example, cluster recognition can be determined as follows. At first, the object wafer is divided into imaginary two-dimensional rectangular areas. Then, each rectangular area is checked as to whether or not a defect exists using the coordinates of a detected defect. A defect found area is substituted for an image of 1 and a no-defect found area is substituted for an image of 0. Next, each image is expanded to determine whether or not the image is connected to another one. And, if the number of defects in the connected area exceeds a threshold value, the area is determined to be high in defect density (cluster presence). In this case, a flag "1" can be set as shown in FIG. 5. However, there are many other methods for cluster recognition, and any of those methods can be used in this example. For example, it is possible to compute a distance between defects by using defect coordinates, thereby to determine defects within a predetermined distance to be cluster.

On the other hand, receiving defect image data 106 shown in FIG. 26, the analysis unit 112 updates the image presence/absence flag 509 to 1 if a defect image exists. The flag 509 which has the same identification information as the object wafer identification information is updated. At this time, the amount in the item "number of inspections" 504 doesn't need to be updated.

On the other hand, receiving probe data 107, the analysis unit 112 increments the item "number of inspections" 504 by one and describes the yield 510 in the list 109 according to the inspection result shown in FIG. 27. Then, just like the defect inspection result processing, the analysis unit 112 describes the process name, the inspection date, the inspection type, and other items specific to the inspection result, for example, presence/absence of cluster and presence/absence of captured image. The inspection type 506 as an electrical inspection is, for example, 2. As for the yield calculation, the number of fail chips in the object wafer is calculated from the probe data, then the number of fail chips as divided by the total number of chips.

Figure 2:
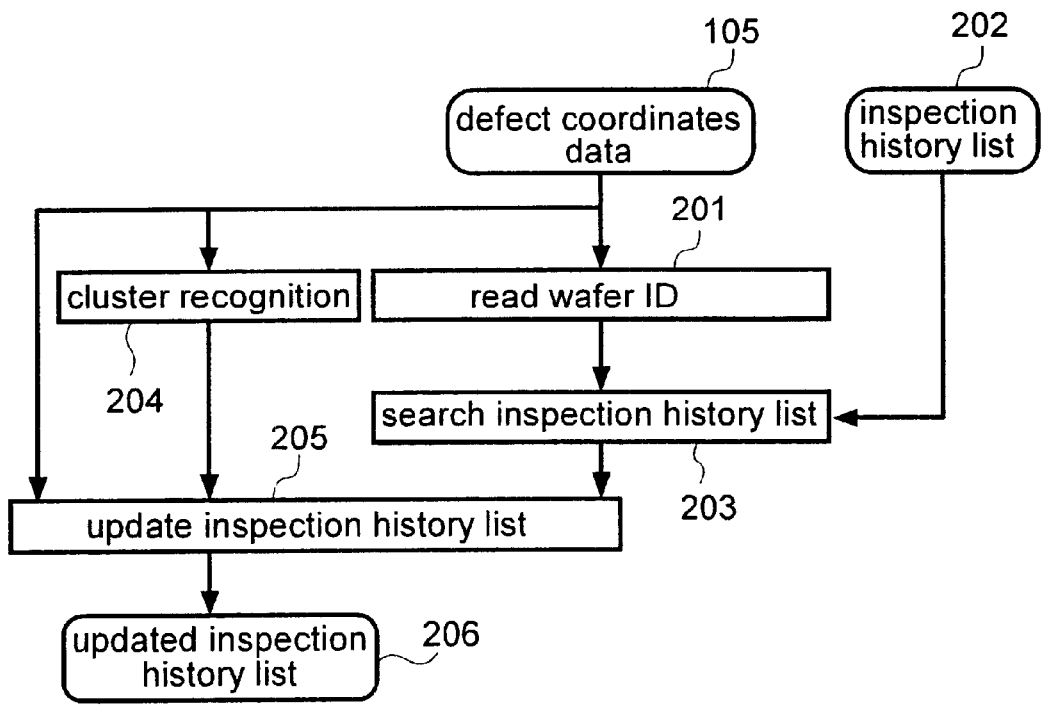
FIG. 2 is a flowchart for creating an inspection history list indicating an example of the present invention.
Figure 3:
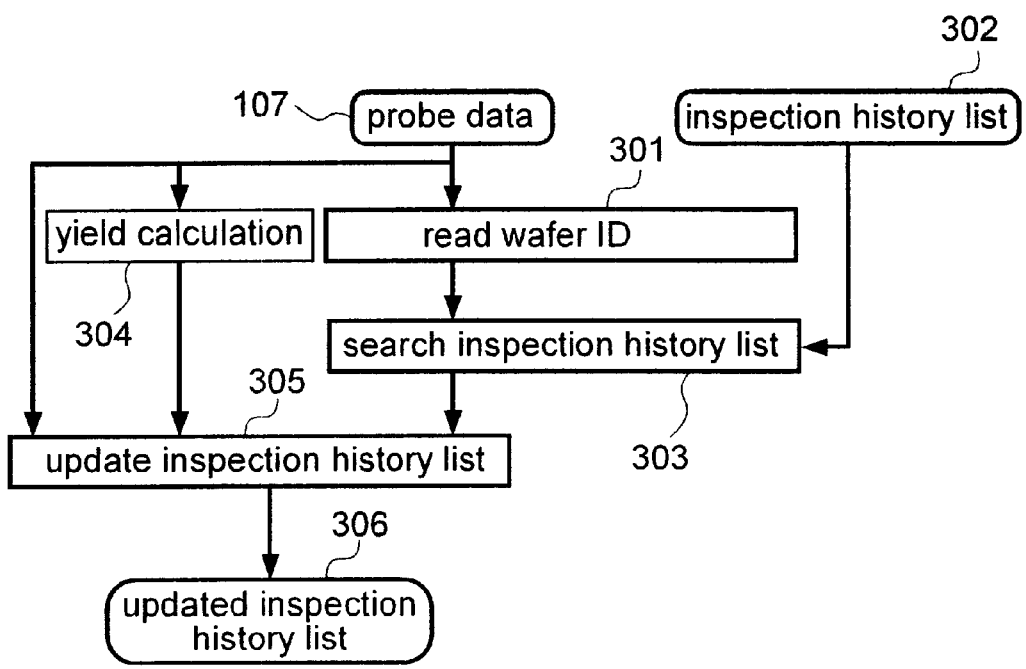
FIG. 3 is a flowchart for creating an inspection history list indicating an example of the present invention.
Figure 4:
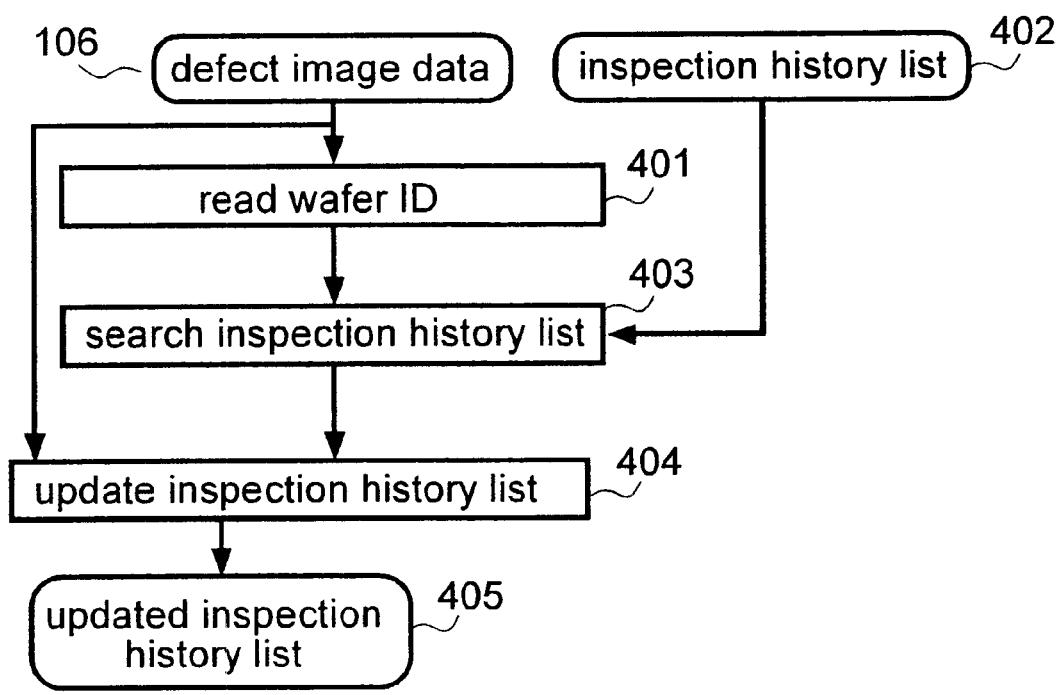
FIG. 4 is a flowchart for creating an inspection history list indicating an example of the present invention.

FIG. 2 through FIG. 4 show the process executed by the analysis unit 112 when receiving a defect inspection result, an observation result, and an electrical inspection result.

As shown in FIG. 2, receiving a defect inspection result such as defect coordinates data 105, the analysis unit 112 reads identification information of the object wafer (step 201) to extract the already created inspection history list 202 including the inspection history of the wafer (step 203). The inspection history list is the same as that shown in FIG. 5. Then, the analysis unit 112 describes the received defect inspection result in the corresponding items of the extracted inspection history list thereby to update the list (step 205). On the other hand, the analysis unit 112 determines whether or not any cluster defects exist on the wafer using the defect coordinate data (step 204), then describes the result processed in the step 204 to the extracted inspection history list thereby to update the list (step 205). The items to be updated or added here are the number of inspections, the process name, the inspection type, the cluster presence/absence information, the inspection date, and the image presence/absence information.

As shown in FIG. 3, receiving an electrical inspection result such as probe data 107, the analysis unit 112 reads the identification information of the object wafer (step 301) to extract the already created inspection history list 302 (step 303). The inspection history list is also the same as that shown in FIG. 5. Then, the analysis unit 112 describes the received electrical inspection result in the corresponding items of the extracted inspection history list thereby to update the list (step 305). On the other hand, the analysis unit 112 calculates a yield using the electrical inspection result (step 304) and describes the result to the extracted inspection history list thereby to update the list (step 305). The items to be updated or added here are the number of inspection, the process name, the inspection type, the cluster absence information, the inspection time, the image absence information, and the yield. The inspection type here means an electrical inspection identifier.

As shown in FIG. 4, receiving an observation result such as defect image data 106, the analysis unit 112 reads the identification information of the object wafer (step 401) to extract the already created inspection history list 402 (step 403). The inspection history list is also the same as that shown in FIG. 5. Then, the analysis unit 112 describes the received observation result in the corresponding items of the extracted inspection history list thereby to update the list (step 404). The items to be updated here is the image presence information.

The above inspection history lists 202, 302, and 402 are actually all the same physical files, but have been described with different numerals for drawing convenience. The inspection history list may be updated each time the analysis unit 112 receives one of the various inspection results or periodically at a predetermined time.

As described above, the analysis unit 112 is composed so as to store various inspection results for each wafer as an inspection history list.

Next, a display example using an inspection history list will be described. This display example will make it easier to select an object wafer to analyze or inspect, thereby to shorten the analyzing time and obtain the desired inspection data effectively.

Figure 6:
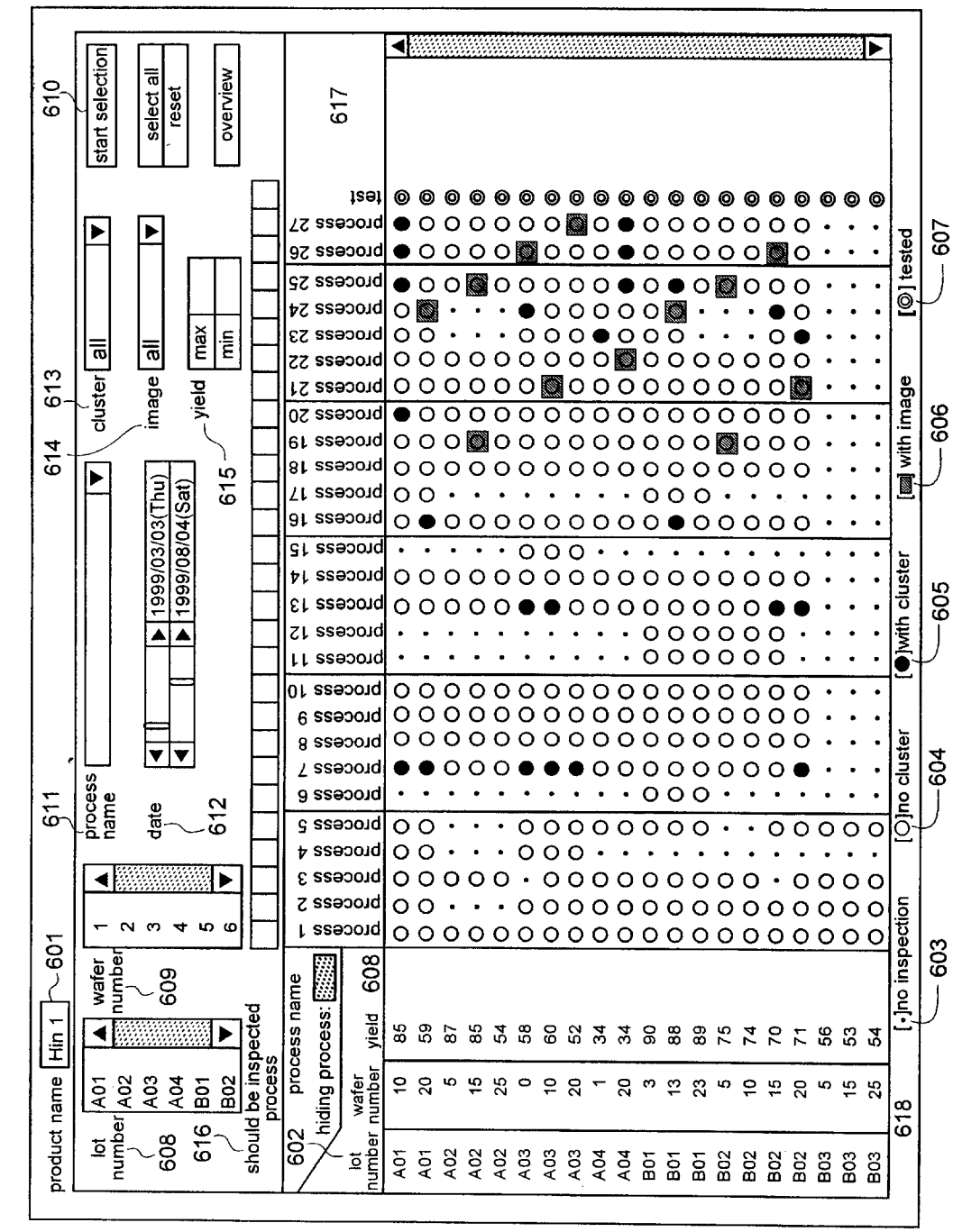
FIG. 6 shows the functions of an analyzing system using an inspection history list indicating an example of the present invention.

FIG. 6 shows a display example (analysis wafer selection page) generated by using information of an inspection history list 109. The lot numbers and the wafer numbers 602 which are able to be analyzed, as well as the inspection history corresponding to the product name 601 inputted by user are displayed. Inspection history includes "no-inspection 603 (black dot)", "no-cluster 604 (single circle)", "with cluster 605 (black circle)", "with image 606 (shaded)", "tested 607 (double circles)", and "yield 608".

The analysis wafer selection page shown in FIG. 6 can be generated easily by using an inspection history list as shown in FIG. 5. For example, the screen can be composed to display all inspection processes selected from an object manufacturing line in a time series at the process indication area 617. And, the screen can be composed to display all identification information items of the object wafer, etc. in the analysis object display area 618. And since each inspection history list describes the identification information of an inspected wafer and its processes to be inspected, etc., the identification numbers such as the wafer number included in the inspection history list may be displayed in the analysis object display area 618 of the analysis wafer selection page. And other information (specific information such as a wafer-inspected process, wafer-not-inspected processes, cluster presence/absence, etc.) described in the inspection history list may be displayed in the analysis display area 618 using given symbols.

One important feature of this analysis wafer selection page is that it provides a display of inspection history of an object wafer in order of the inspection process so as to identify easily in which process the object wafer was inspected.

Another important feature of this analysis wafer selection page is that it also provides a display of the items (presence/absence of cluster, presence/absence of captured image, and electrical inspection) specific to the inspection result.

Another important feature of this analysis wafer selection page is that it permits a search by using the above displayed items and an analysis by using the results of the search.

This analysis wafer selection page makes it possible to display how an object wafer has been inspected, which has been impossible for the conventional analyzers to know. Consequently, it is now possible to select a desired wafer suitable for a particular type of object analysis. This also makes it possible to analyze the inspection results including only peculiar items such as cluster defects, or, on the other hand, to analyze the inspection results without any particular items, respectively. Thereby, it is now possible to select the inspection results according to the purpose of analysis and analyze them accordingly. As a result, the analyzing accuracy is improved. In other words, this analysis wafer selection page makes it easy to select a proper wafer according to the purpose of analysis, thereby to shorten the analyzing time and to obtain the desired inspection data effectively.

Next, various searching methods, which use the analysis wafer selection page shown in FIG. 6, for narrowing an object wafer down according to the analysis content are explained.

At first, the analysis wafer selection page shown in FIG. 6 is provided with a function for searching a corresponding lot number 608 and a corresponding wafer number. 609 according to a inputted lot number and a inputted wafer number which numbers are inputted by a user, a function for searching corresponding wafers which are processed in the inputted specified process and are processed within an inputted specified period which are also inputted by a user, a function for searching corresponding wafers on which no cluster is detected in any processes, a function for searching corresponding wafers in which defect images are captured, a function for searching corresponding wafers having a yield within a predetermined value, and a function for searching corresponding wafers inspected in a specified process.

Any of those searching functions are composed to extract the corresponding object inspection results from the inspection history list according to inputted searching conditions. Furthermore, search keys can be provided for the functions described above including a lot number 608, a wafer number 609, a process name 611, an inspection date 612, cluster presence/absence information 613, image presence/absence information 614, a yield 615, and a mandatory inspection process 616, and a plurality of keys can be used for such a searching.

Next, a defect location history list 111 used for creating various analysis pages will be described. Unlike the inspection history list 109 described above, a defect location history list 111 stores inspection results for each wafer respectively(1 list/1 wafer). Such a defect location history list 111 can process data effectively for generating various analysis pages. Consequently, if no effective analysis is needed, it is not necessary to use such a defect location history list 111 specially.

FIG. 9 shows a configuration of such a defect location history list 111. The defect location history list 111 is a collection of various types of inspection data for each wafer(1 list/1 wafer). The collection of inspection data includes the coordinates of each defect generated on an object wafer, its attribute items such as the defect detected process, the number of defects existing in the proximity of predetermined defect coordinates, defect size, defect category, cluster information, and captured image index information. A defect location history list 111 is created as follows for each wafer(1 list/1 wafer).

At first, in the top portion of the list are described items of wafer identification information (901 to 903), a defect location history list creating parameter 904, and an inspection process name 905. The wafer identifiers in FIG. 9 are a type 901, a lot number 902, and a wafer number 903. The parameter 904 is a parameter for cluster recognition and an added defect recognition (i.e., the recognition of new defects). In the inspection process name 905, the processes are described in the order in which the wafer was inspected. In FIG. 9, there are three inspection processes. The inspection date 913 is a date on which the object wafer was inspected.

Next, each of the defects which are detected newly between process 1 to 3 are described as the defect coordinates 906. In this example, the coordinates of defects which are detected in the process 1 are described just as its result. However, in the second and subsequent processes, the coordinates of only the defects determined as not matching with the coordinates of the defect detected in the process 1 are described sequentially. "Matching" mentioned here means matching within a predetermined allowable range; it does not mean perfect matching.

Then, the "defect count in each process" 907 is filled, indicating how many defects are found in each process with respect to the coordinates of each of the defects. The detected defect count in each of the processes 1, 2, and 3 is described sequentially from left to right. The detected defect count "2" means that two defects exist within a predetermined radius around the defect coordinates 906. In FIG. 9, some defects are detected in the process 1 and not detected in the process 2 and after. Some defects are detected in all the processes and others detected in the process 1 are not detected in the process 2, but detected again in the process 3. In this example, the number of defects detected in each process is just described corresponding to the predetermined defect coordinates.

The display of the defect generated process 908 makes it easier to understand the ""defect count in each process" 907". In this example, "0" means that defect is detected for the first time in the process 1, and "1" means that defect is detected for the first time in the process 2, "2" means that defect is detected for the first time in the process 3. And "255" means that no defect is detected in the proximity of the corresponding coordinates.

The defect size 909 displays sizes of the defects detected. In this example, each defect size is indicated as 1, 2, or 3. The larger the number is, the larger the defect is in size. The real size is also acceptable instead of 1,2,3.

The defect category 910 indicates a result of defects classified by predetermined category. In this example, 1 to 9 are used for classifying defects.

The cluster 911 indicates a result of determination for the density of defect coordinates. A unique identification number is given to each cluster and such a cluster number is given to the coordinates of each defect.

The image index 912 indicates an index of each defect image captured in each process. Numbers disposed side by side indicate that an image of the defect is captured sequentially in each of the processes. In this example, a large size defect is selected and its image is captured.

As described above, the defect location history list 111 comprises the coordinates of each defect detected on a wafer and the attribute items of the coordinates, such as defect the detected process, detected defect count, defect size, defect category, cluster information, and captured image index information. This list 111 can list all the past information of each defect on an object wafer. Therefore, by referencing to, for example, the defect coordinates 906 and the "defect count in each process" 907, a defect map gallery can be displayed in order of inspection process as shown in FIG. 10.

In the same way, by referencing to the defect coordinates 906 and the defect generated process 908 and drawing only the coordinates of defects newly detected in each process (i.e., added defects), it is possible to display the added defect map of each process. It is also possible to reference to the cluster information 911 thereby to display how a cluster is generated in each process. In this way, a defect location history list 111 contains every type of information of every defect on every wafer, so that the list is very useful for checking defects on a wafer totally.

Figure 11:
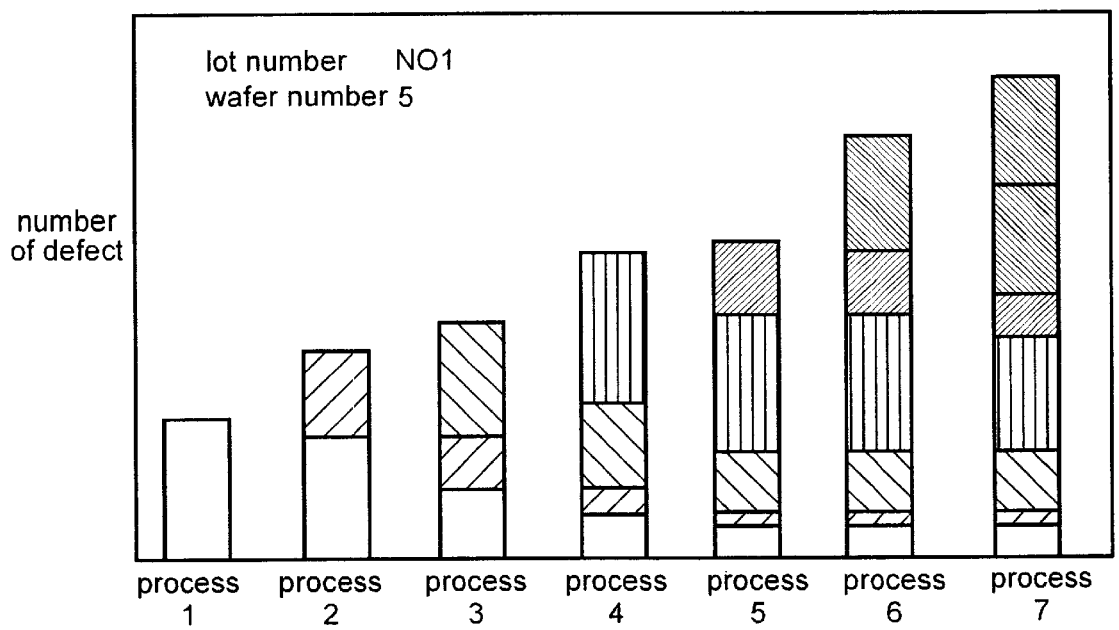
FIG. 11 shows the functions of an analyzing system using a defect location history list indicating an example of the present invention.

Furthermore, by referencing to the defect generated process 908 and displaying the detected "defect count in each process" with a vertical bar graph (stack chart) for each defect generated process, it is possible to know how defects caused by each process are generated and how those defects are detected in the subsequent processes at a glance (FIG. 11). Such a bar graph can be obtained by a process tracing operation. A process tracing operation means discriminating some defects (added defects) which have appeared for the first time in the process. In this operation, inspection data is compared with each added defect of the previous processes sequentially, thereby to recognize that the defects that are not within a predetermined distance from the coordinate of the added defect coordinates of the previous processes as added defects of the object process. This predetermined distance is called a comparison radius. In a defect location history list 111, a defect generated process is discriminated for each added defect beforehand, so that it is very easy to obtain the result of a process tracing operation. Accordingly, all the defect history information of an object wafer can be obtained easily by referring to the corresponding list of the defect location history list 111. And searching and calculating of data for analysis are arranged beforehand, thereby to shorten the preparing time for analysis significantly. In other words, conventionally, analyzing has been made by searching a necessary inspection result after receiving an analytic command from an analytic terminal. For example, in the case of process tracing, it took a full day (24 hours) of analyzing the inspection results when an instruction was issued to make, for example, an analysis of one week of data. In this embodiment, however, necessary processing (outside arrangement of searching and calculating of data for analysis) for an object analysis is executed before such an instruction is received, that is, each time an inspection result is sent to the analysis unit, and the inspection result is stored beforehand as shown in FIG. 9. Accordingly, the conventional analyzing time could be reduced significantly (for example, from 24 hours to 10 minutes).

Figure 7:
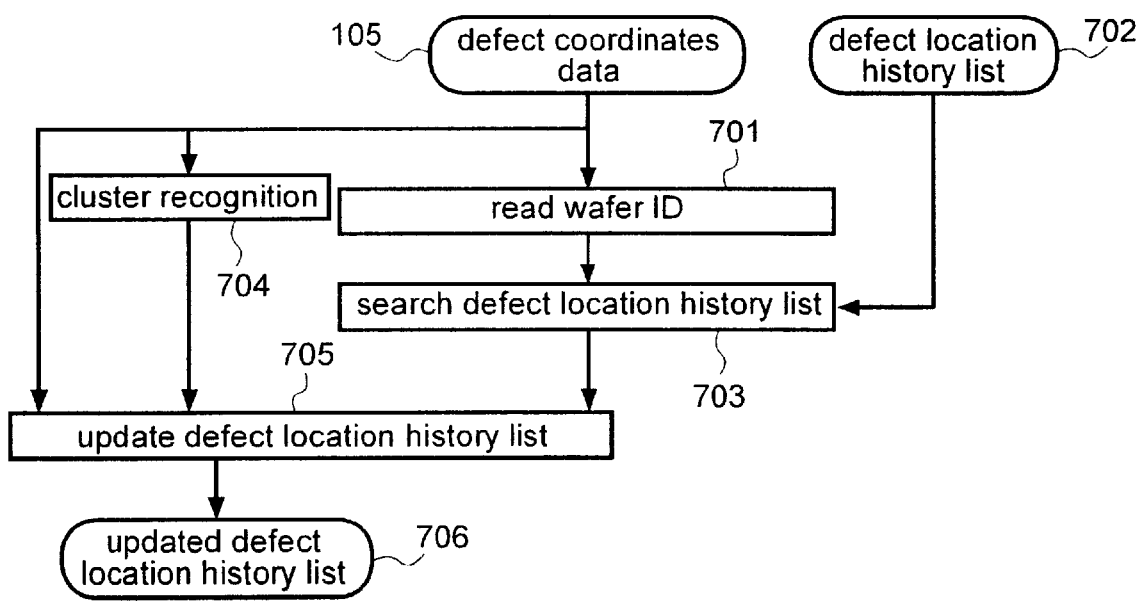
FIG. 7 is a flowchart for creating a defect location history list indicating an example of the present invention.
Figure 8:
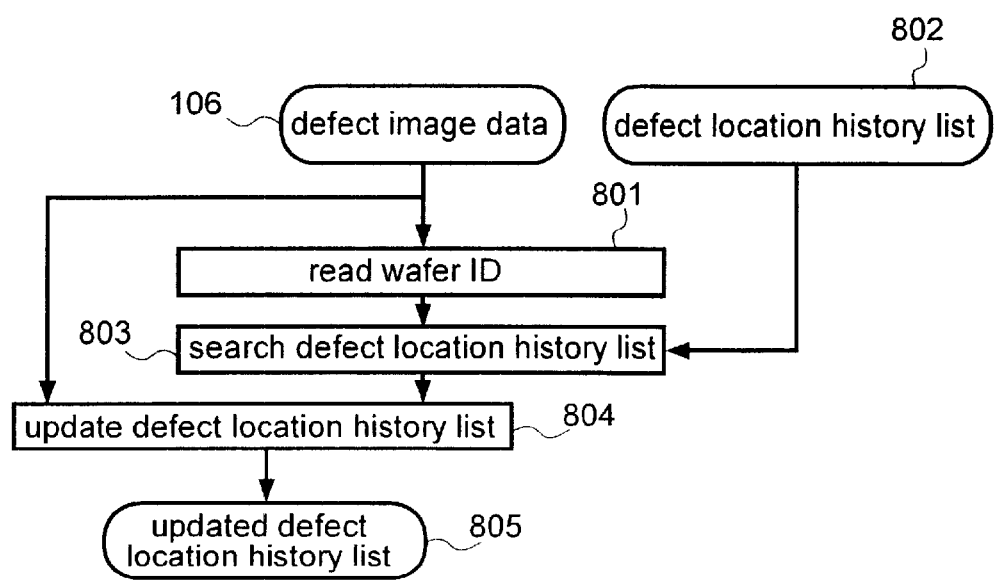
FIG. 8 is a flowchart for creating a defect location history list indicating an example of the present invention.

FIG. 7 and FIG. 8 show an example of a transaction of making the defect location history list 110 in the analysis unit 112.

Receiving defect coordinate data 105, the analysis unit 112 reads the identification information of the object wafer (step 701) to extract the already created defect location history list 702 as shown in FIG. 9 using the wafer identification information (step 703). Then, the analysis unit 112 updates the defect location history list 702 (step 705). In other words, the analysis unit 112 updates the defect location history list 702 using the defect inspection results shown in FIG. 25. Furthermore, the analysis unit 112 does the cluster recognition using the defect inspection result shown in FIG. 25 (step 704), then updates the defect location history list 702 using the recognition result (step 705). The items to be updated and added in this processing are the coordinates of each newly detected defect and the attribute items such as the defect detected process identifier, detected defect count, defect size, defect category, cluster identification information, and an image index absence flag, as well as an attribute item added to the coordinates of each of the already-detected defects, such as the defect detected process identifier, detected defect count, defect size, defect category, cluster identification information, and an image index absence flag.

In the same way, receiving the defect image data 106, the analysis unit 112 in FIG. 8 reads the identification information of the object wafer (step 801) to extract the already created defect location history list 802 as shown in FIG. 9 (step 803). Then, the analysis unit 112 updates the defect location history list 802 (step 804). In other words, the analysis unit 112 updates the defect location history list 802 using the defect observation result shown in FIG. 26. The item to be updated in this processing is the captured image index corresponding to the defect image captured process.

The defect location history list, just like the inspection history list, is generated using the defect inspection result and the defect observation result shown in FIG. 25 and FIG. 26. The defect location history lists 702 and 802 are the same for each wafer respectively.

Figure 12:
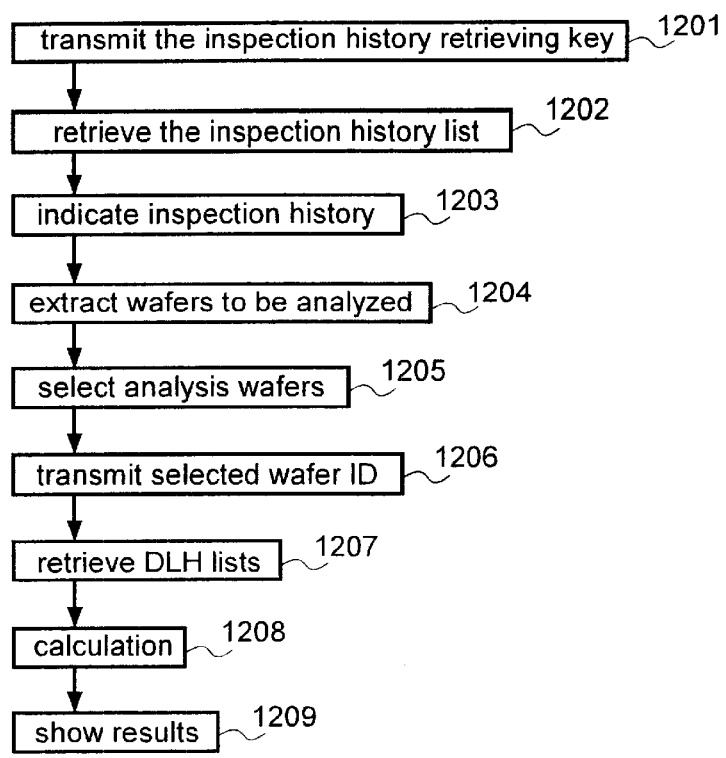
FIG. 12 is a flowchart for the operation of an analyzing system indicating an example of the present invention.

Next, description will be made for an example of an analyzing operation using an inspection history list 109 and a defect location history list 111 described above. FIG. 12 shows a processing flow of the data analysis terminal 113 in such a case.

The data analysis terminal 113 transmits an inspection history list retrieving key to the analysis unit 112 at first (step 1201) to retrieve an object inspection history list (step 1202). Then, the data analysis terminal 113 displays the inspection history to analyze (step 1203), narrows the group of possible object wafers down using the displayed inspection history (step 1204), and then selects the object wafer (step 1205). The data analysis terminal 113 transmits the identifier of the selected wafer to the analysis unit 112 (step 1206) to retrieve the defect location history list (step 1207). The data analysis terminal 113 then refers to the defect location history list to compute data according to the analytic purpose (step 1208) and display the result (step 1209).

Figure 13:
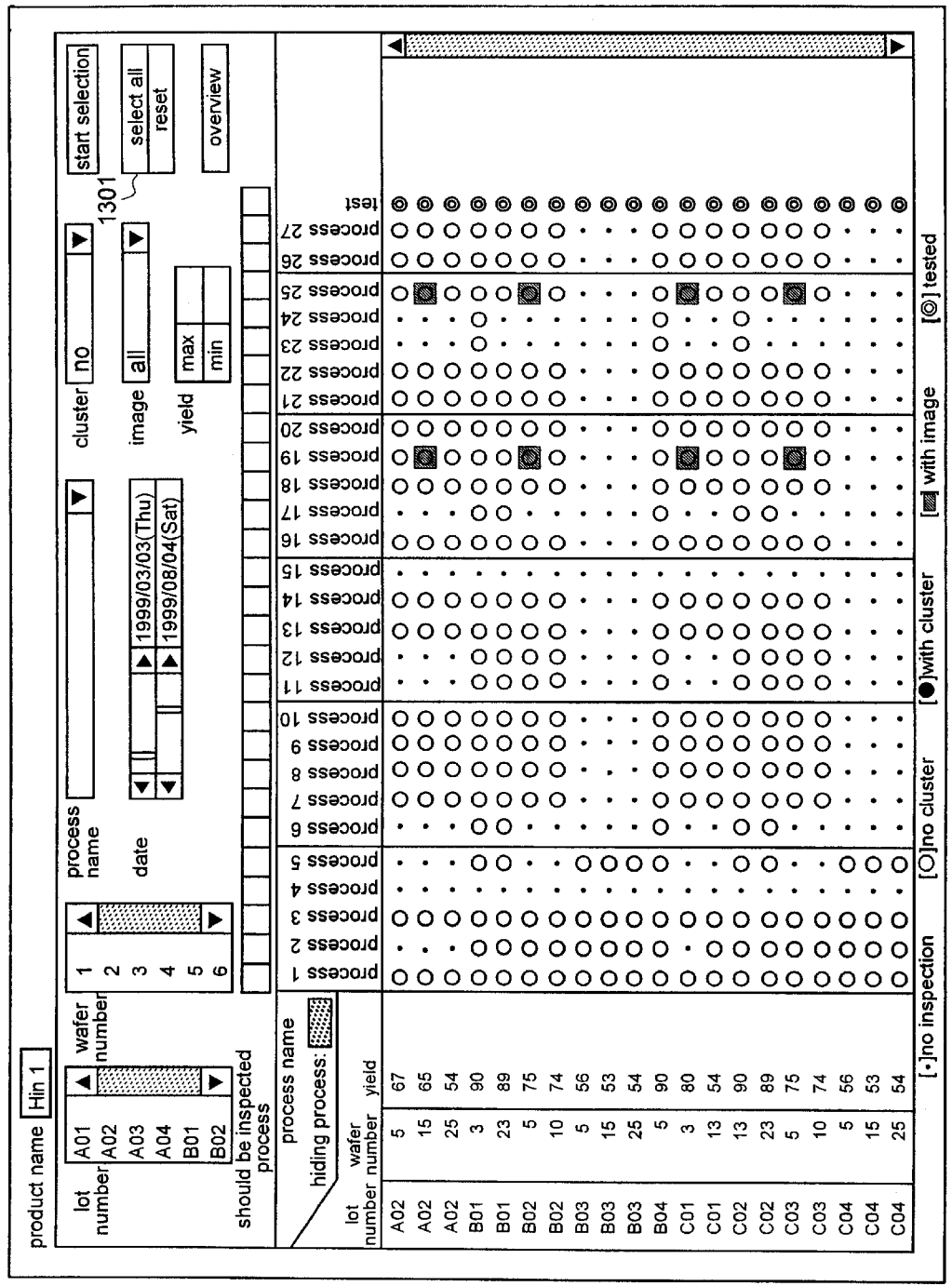
FIG. 13 shows the functions of an analyzing system using an inspection history list indicating an example of the present invention.

FIG. 13 shows a result of searching wafers having no cluster from the list of object wafers to analyze shown in FIG. 6. If processes 4, 15, 23, and 24 are selected as "hiding" processes, then the "SELECT ALL" button 801 is pressed, and all the displayed wafers (except for processes 4, 15, 23, and 24) are selected as objects to analyze.

Figure 14:
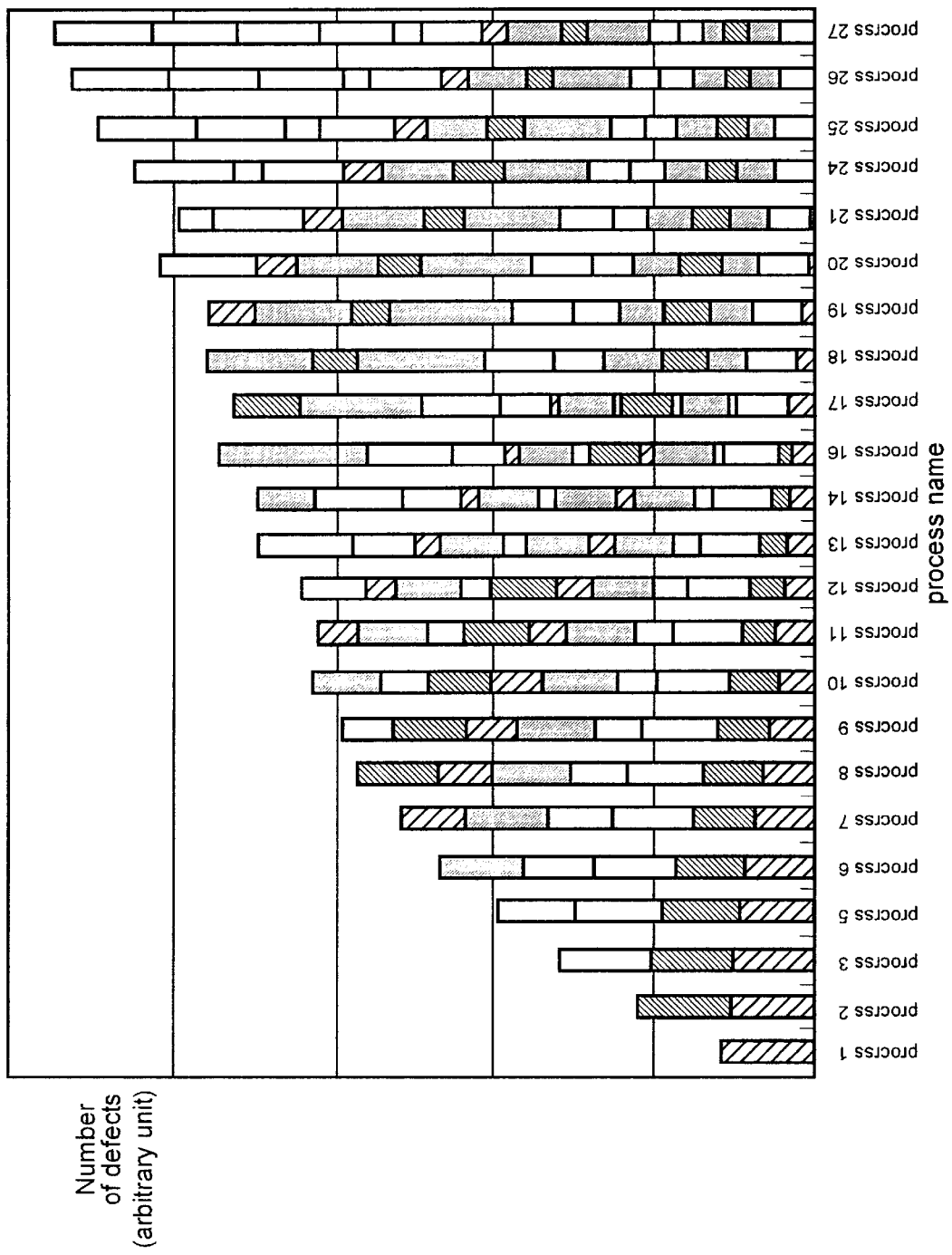
FIG. 14 shows the functions of an analyzing system indicating an example of the present invention.

FIG. 14 shows a result of averaging the values in the stack chart of each wafer by referring to the defect location history lists of those object wafers. Since processes 4, 15, 23, and 24 are selected as hiding process steps on the object wafer select screen, those processes are not displayed in any stack charts.

Selecting hiding process steps in such a way will bring the following effects. The number of added defects in the process 25 in which wafers are inspected in the processes 23 and 24 and the number of added defects in the process 25 in which wafers are not inspected in those processes are different. That is, if the wafer is not inspected in the processes 23 and 24, the defects that should be identified as added defects in the processes 23 and 24 respectively are counted as added defects in the process 25. This is why these numbers of added defects are different. Such a difference between calculating conditions in the process tracing, which is caused by a difference of each wafer inspection process from others, becomes a factor of big deviations for averaging of results of the process tracing. Consequently, it is assumed that no inspection is made in the processes selected as hiding processes and then the number of the added defects in the hiding processes are added to number of the added defects in the next processes to the hiding processes so as to improve the analyzing accuracy.

In addition, cluster-detected wafers could be excluded from analysis. In other word, special wafers, which are expected to increase the defect count significantly such as having handling errors or loading trouble, could be excluded from analysis automatically. Consequently, it is possible now to make the accuracy of process tracing higher, as well as to know how much dust is generated in each process, that is, to know the real number of defects more accurately.

Figure 15:
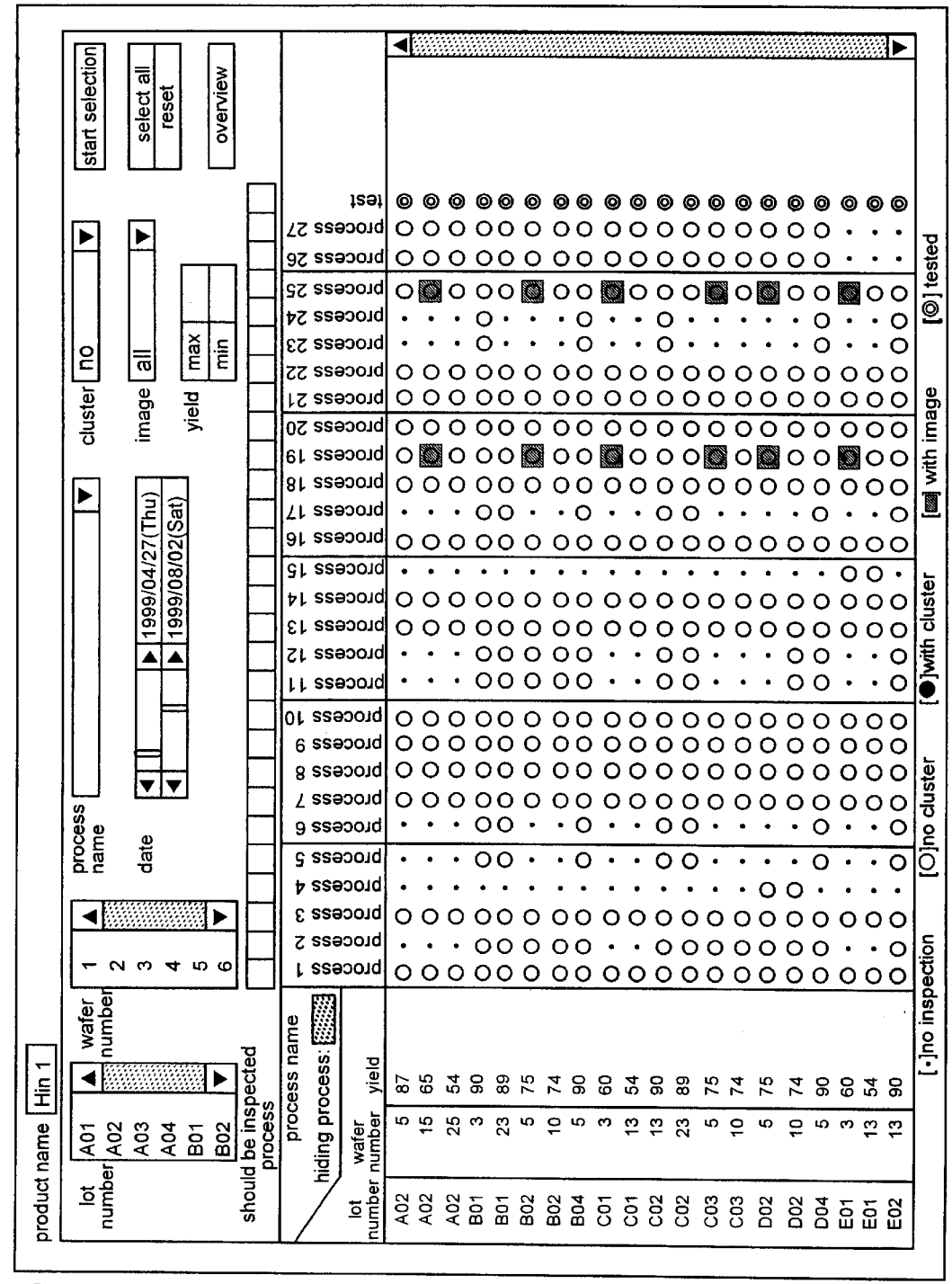
FIG. 15 shows the functions of an analyzing system using an inspection history list indicating an example of the present invention.

FIG. 15 shows a result of searching no-cluster-detected wafers in all the processes. The objected wafers were inspected in the process 21 in a test run over a 14 week period.

Figure 16:
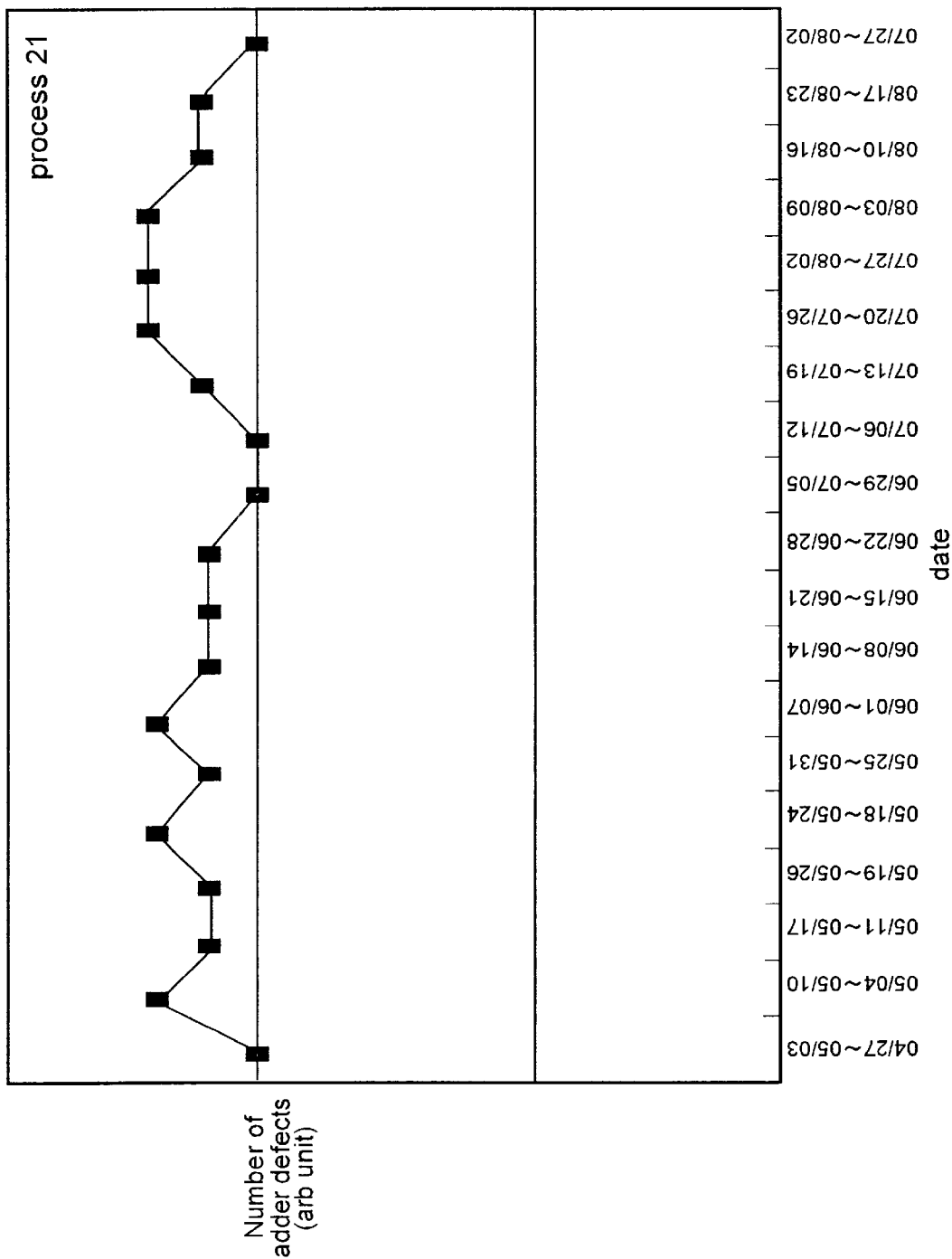
FIG. 16 shows the functions of an analyzing system indicating an example of the present invention.

FIG. 16 shows a result of weekly calculation/display of the changes of the added defect count in the process 21 by referencing to the defect location history lists 111 of the object wafers. Each defect location history list 111 describes the inspection date and the added defects pre-calculated in each process. It is thus very easy to obtain the items shown in FIG. 16. And, since cluster-detected wafers are excluded from analysis, it is possible now to make the accuracy of process tracing higher, as well as to know how much dust is generated in process 21, thereby to make process control more accurately.

Figure 17:
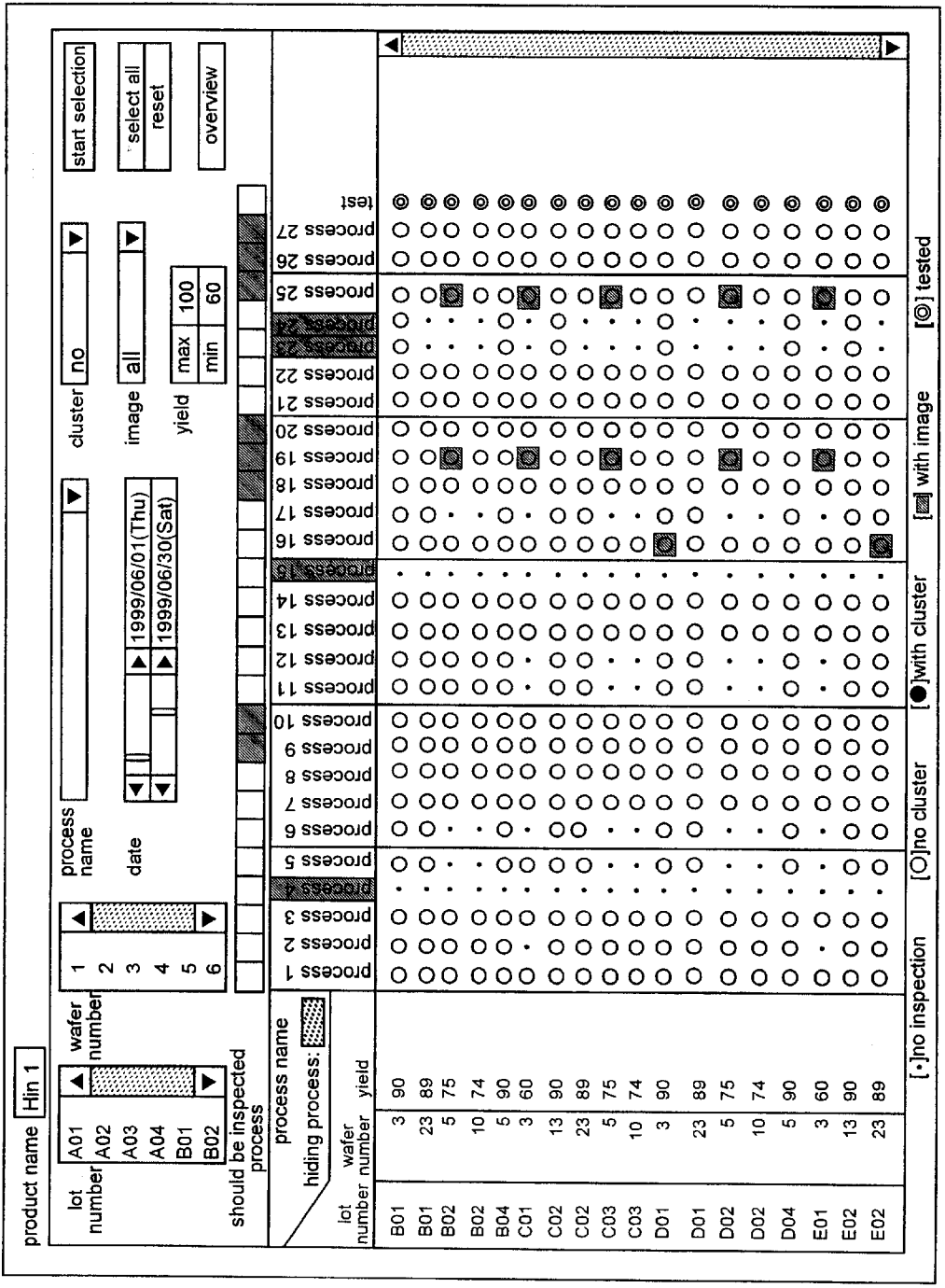
FIG. 17 shows the functions of an analyzing system using an inspection history list indicating an example of the present invention.

FIG. 17 shows a result of searching of wafers inspected in the process 9, 10, 18, 19, 20, 25, 26, and 27. The wafers were finished over a one month period. The wafers were applied with a probe test and had a yield of 60% or over and no clusters detected in any processes. Processes 4 and 15 in which the wafers were not inspected, as well as steps 23 and 24 in which less wafers were inspected were specified as hiding process steps. Then, the "SELECT ALL" button was pressed. The defect location history lists 111 of those wafers are referenced to correlate between the result of the probe test as to the chip and the added defects.

Figure 18:
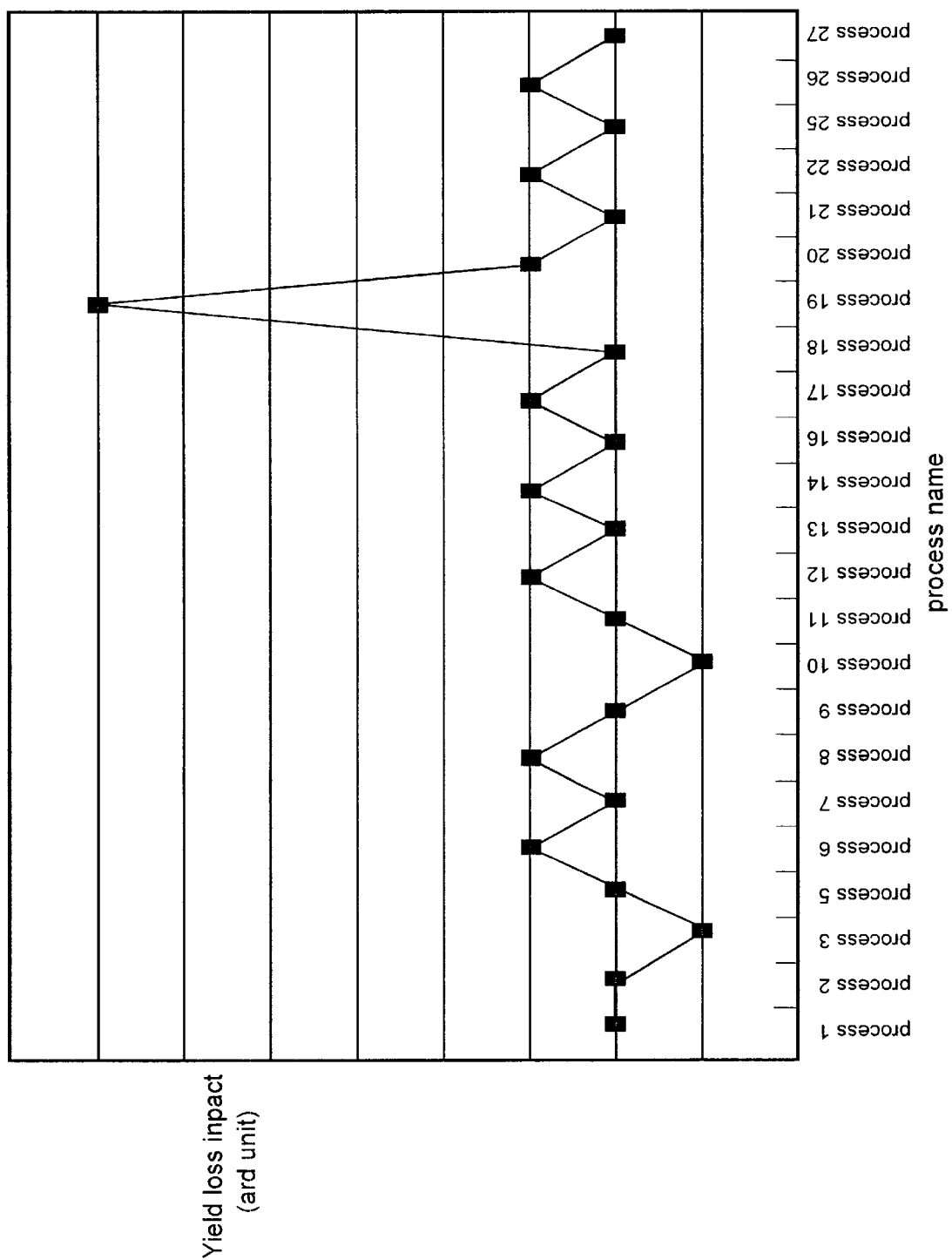
FIG. 18 shows the functions of an analyzing system indicating an example of the present invention.

FIG. 18 shows results of calculation and display of how much the defects affect the yield in each process. Cluster-detected wafers and low yield wafers were excluded from analysis, since they would become factors causing a big deviation in analysis of correlation between the defects and the yield. Thus, the analytic reliability has been improved significantly. In addition, since a mandatory inspection process was selected to narrow the number of object wafers to analyze, the number of data items to analyze was increased in each object process in the analysis, so that the reliability of the statistical analysis result was improved. In addition, since processes in which less wafers were inspected were specified as hiding process steps and excluded from analysis, and the same conditions for calculating the added defects in the next process were set for all wafers, the analytical calculation accuracy was improved. Consequently, it is now possible to accurately know how much defects caused by each process affect the yield, as well as to improve the accuracy for setting priorities of processes coping with defects. In addition, it is now possible to know the capability of the object manufacturing process within a limited time, since the time when object wafers were finished is identified. Since each inspection history list includes all the past inspection information of each object wafer, it is very easy to narrow the number of possible object wafers down according to the analytic purpose.

Figure 19:
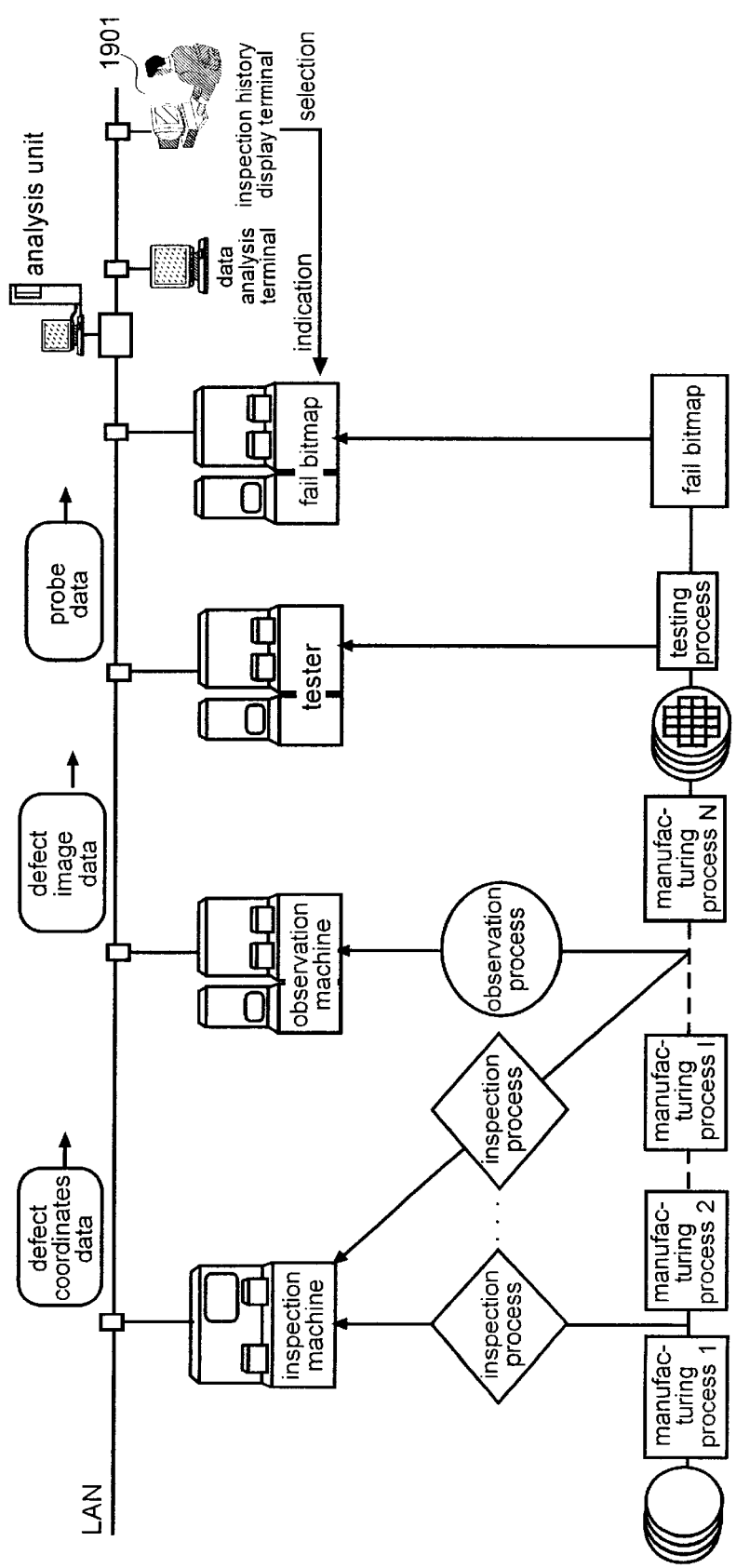
FIG. 19 shows a configuration of an inspection history display system using an inspection history list indicating an example of the present invention.

Next, FIG. 19 shows an example that an inspection history list 109 is transmitted to and referred to on an inspection history display terminal 1901. Finished wafers are functionally tested by a tester. At that time, each chip of a finished wafer is examined to determine if it is conforming/non-conforming. Then, if a more detailed analysis is needed for the wafer, the wafer is tested again for getting a fail bit map. A fail bit map is a map on which a conforming/non-conforming state is displayed for each bit of an object memory. Since making of a fail bit map needs a functionality test bit by bit, it takes a considerably long time for testing one wafer. Consequently, it is very important to select a suitable object wafer. If a suitable one is not selected, we need to test one more wafer and to take a long time for testing again. In other words, an object wafer must be selected from many wafers appropriately to a detailed electrical analysis. Such an object wafer must also satisfy conditions that comparatively much inspection data is collected in manufacturing processes and that process tracing calculation is possible for the wafer. The inspection history display terminal 1901 searches an inspection history list 109 in the analysis unit and obtains it therefrom according to the fail bit inspection object, for example, the type information. The inspection history display terminal can refer to the inspection history of each wafer described in its inspection history list, so that it can select an object wafer for which a fail bit map is to be obtained.

Figure 20:
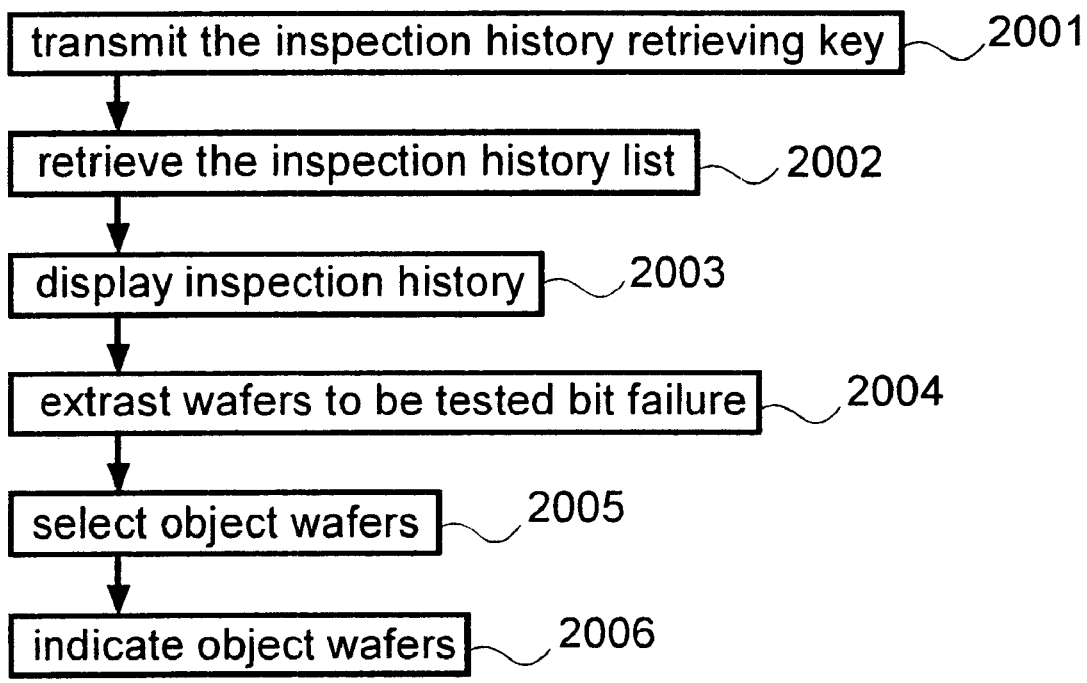
FIG. 20 is a flowchart for selecting a wafer for which a fail bit map indicating an example of the present invention is to be obtained.

FIG. 20 shows a flowchart of a wafer selection so as to obtain a fail bit map. The inspection history display terminal 1901 transmits an inspection history list retrieving key to the analysis unit (step 2001) thereby to retrieve the inspection history list (step 2002). Then, the terminal 1901 displays the inspection history of the object wafer (step 2003) and narrows the group of wafers for which a fail bit map is to be obtained (step 2004), then selects the object wafer (step 2005). The terminal 1901 then transmits the identifier of the selected wafer to the tester(step 2006).

Figure 21:
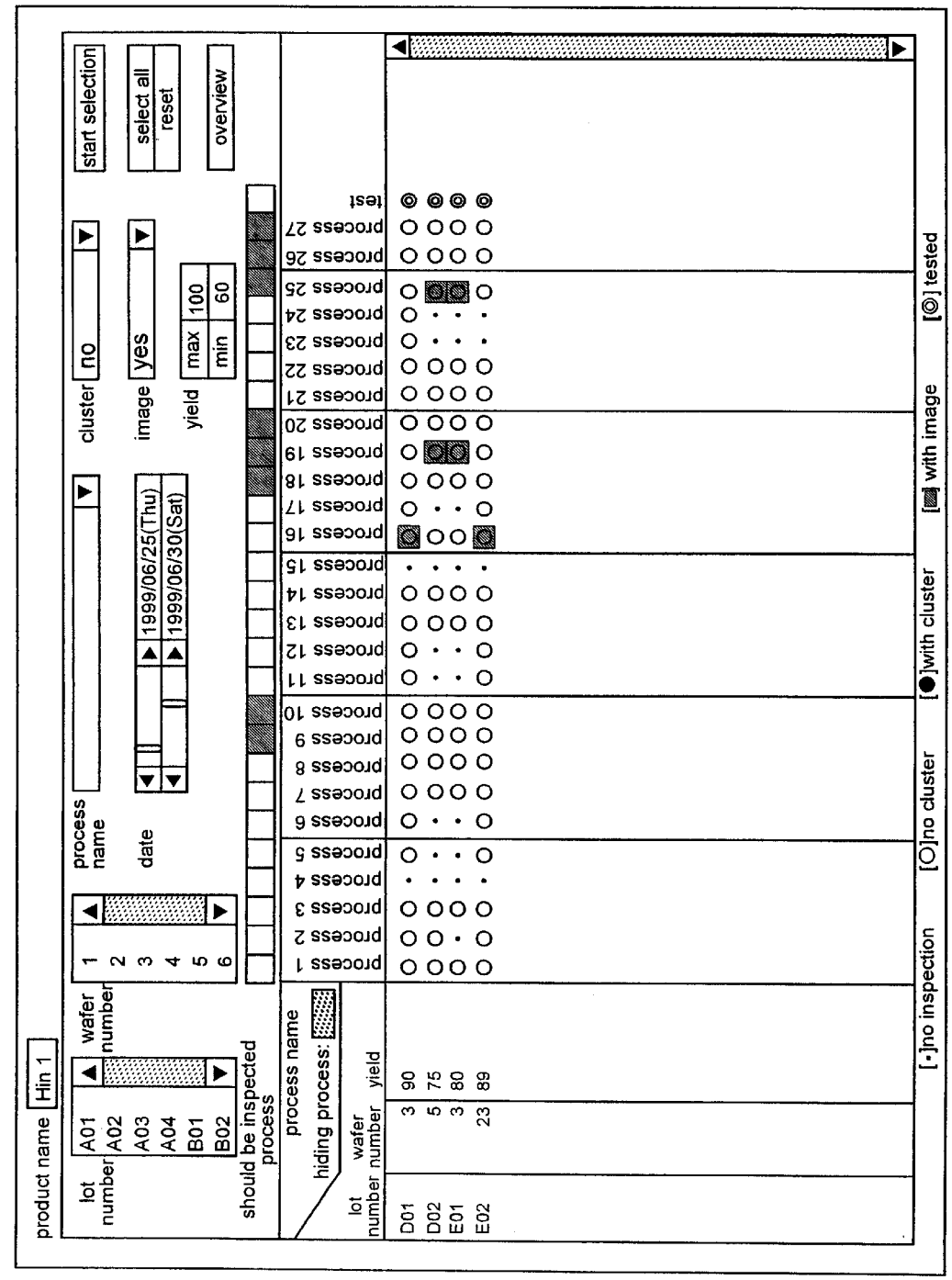
FIG. 21 shows a function for displaying inspection history using a defect location history list indicating an example of the present invention.

FIG. 21 shows an example of a Graphical User Interface of the inspection history display terminal 1901. FIG. 21 shows the result to be narrowed for selecting the wafers to make a fail bit map. Those wafer were delivered between June 25 and 30, and each of the wafers had no cluster and its yield was 60% or over, and its defects were already photographed and stored. If a lot number D01 and a wafer number 3 is selected from those wafers, which is the wafer inspected in the most processes, and if one obtains the fail bit map based on this wafer, it is thus possible to compare positions between a fail bit and a added defect, as well as to refer to defect images in a step considered to cause the fail bit. Since such an inspection history list includes the complete information of the past inspections of the object wafer, it is possible to select a suitable wafer for obtaining a fail bit map by referring to the inspection history list.

In this embodiment, the inspection history display terminal 1901 is referred to select an object wafer for obtaining a fail bit map. However, it is also possible to provide the tester with a function for searching the inspection history list in the analysis unit thereby to display the inspection history.

Figure 22:
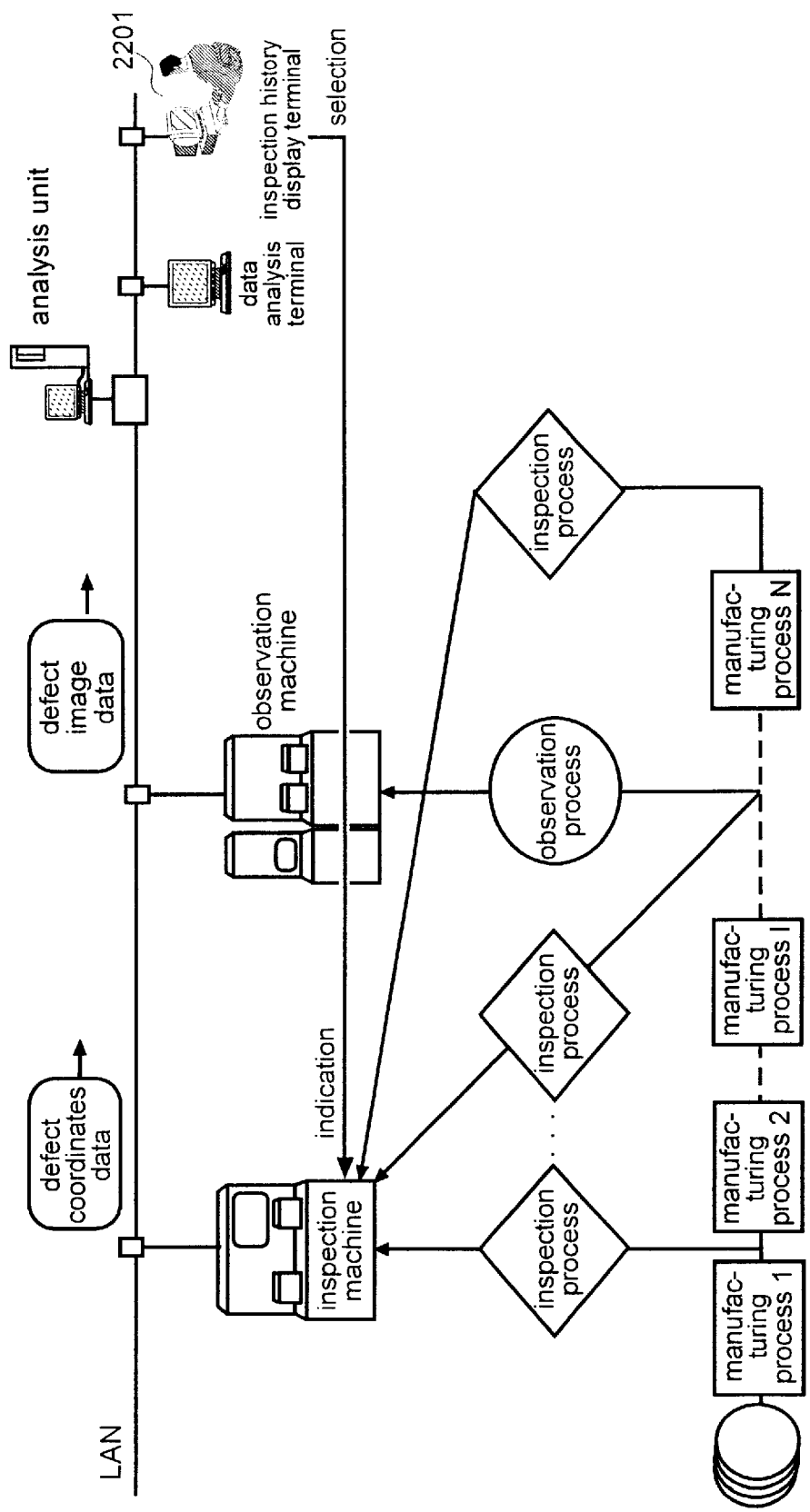
FIG. 22 shows a configuration of an inspection history display system indicating an example of the present invention.

Next, FIG. 22 shows an example that the inspection history display terminal can select an object wafer by referencing to the inspection history list while the wafer is being manufactured. As described above, a process tracing method is very effective for managing manufacturing processes and failure analysis of semiconductors, for example, for recognizing the added defects in each process through process tracing calculation, for estimating a yield loss impact in each process from the correlation between a position of each chip including added defects and results of probe tests, and for narrowing a defect-caused process down by comparing an added defect position with the coordinates of a failure bit in the fail bit map. However, it is very difficult to do a process tracing inspection in a production line that treats a mass of wafers every day. Even when the wafers to inspect are decided beforehand, if wafers for a process tracing inspection have to be changed due to a problem, it will also be difficult to set other wafers for process tracing inspection in a production line consisting of hundreds of manufacturing processes.

To avoid such troubles in this example, therefore, the inspection history list of wafers in an object lot can be referred to at the inspection history display terminal thereby to make it easier to select object wafers for the next inspection. For example, by referencing to the inspection history described in the inspection history lists, we can see which wafers have been inspected continuously so far.

Figure 23:
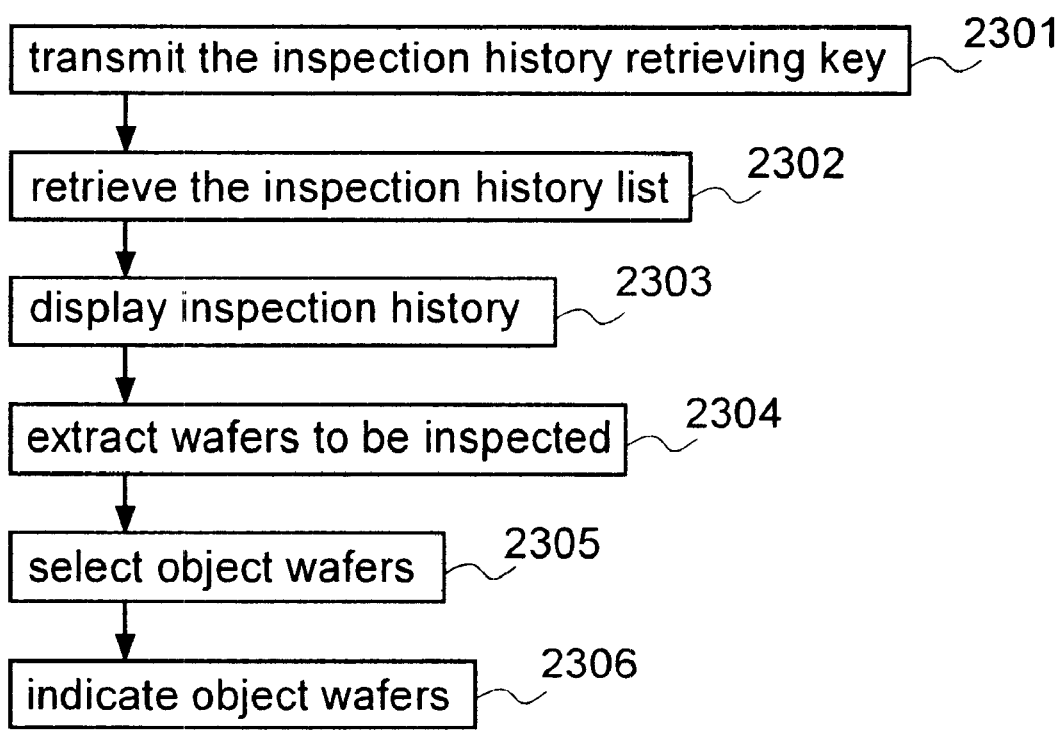
FIG. 23 is a flowchart for selecting a wafer to be inspected indicating an example of the present invention.

FIG. 23 shows a flowchart for selecting a wafer to inspect. The inspection history display terminal 2201 transmits an inspection history list retrieving key to the analysis unit (step 2201) thereby to retrieve the object inspection history list (step 2202). Then, the terminal 2201 displays the inspection history of the object wafer (step 2203) and narrows the group of possible object wafer down (step 2204), and then selects the object wafer (step 2205). After this, the terminal 2201 notifies the analysis unit of the identifier of the selected wafer (step 2206).

Figure 24:
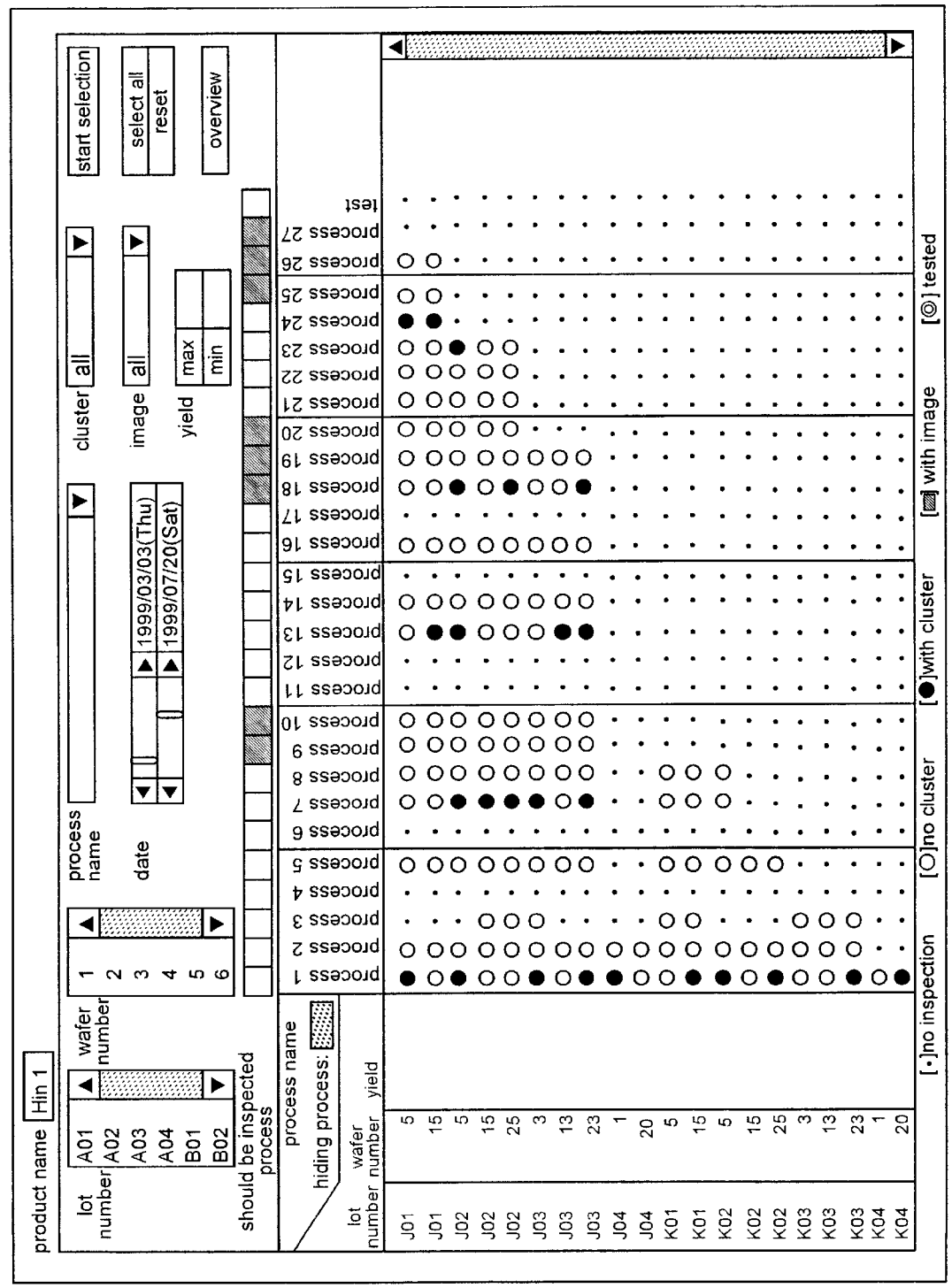
FIG. 24 shows a function for displaying inspection history using a defect location history list indicating an example of the present invention.

FIG. 24 shows an example of the GUI of the inspection history display terminal 2201. FIG. 24 shows which of the wafers in each lot is inspected in which of the processes. If a lot number is specified at this display, the process tracing states of the wafers of the specified lot are displayed. Then, the suitable object wafer can be selected according to this information. Consequently, a specific wafer can be inspected consistently in many processes, thereby to improve the efficiency and reliability of collected inspection data.

In this embodiment, the inspection history list in the analysis unit are searched from the inspection history display terminal 2201. However, instead of the inspection history display terminal 2201, the inspection machine can have a function for searching the inspection history list in the analysis unit and obtaining it therefrom.

Figure 28:
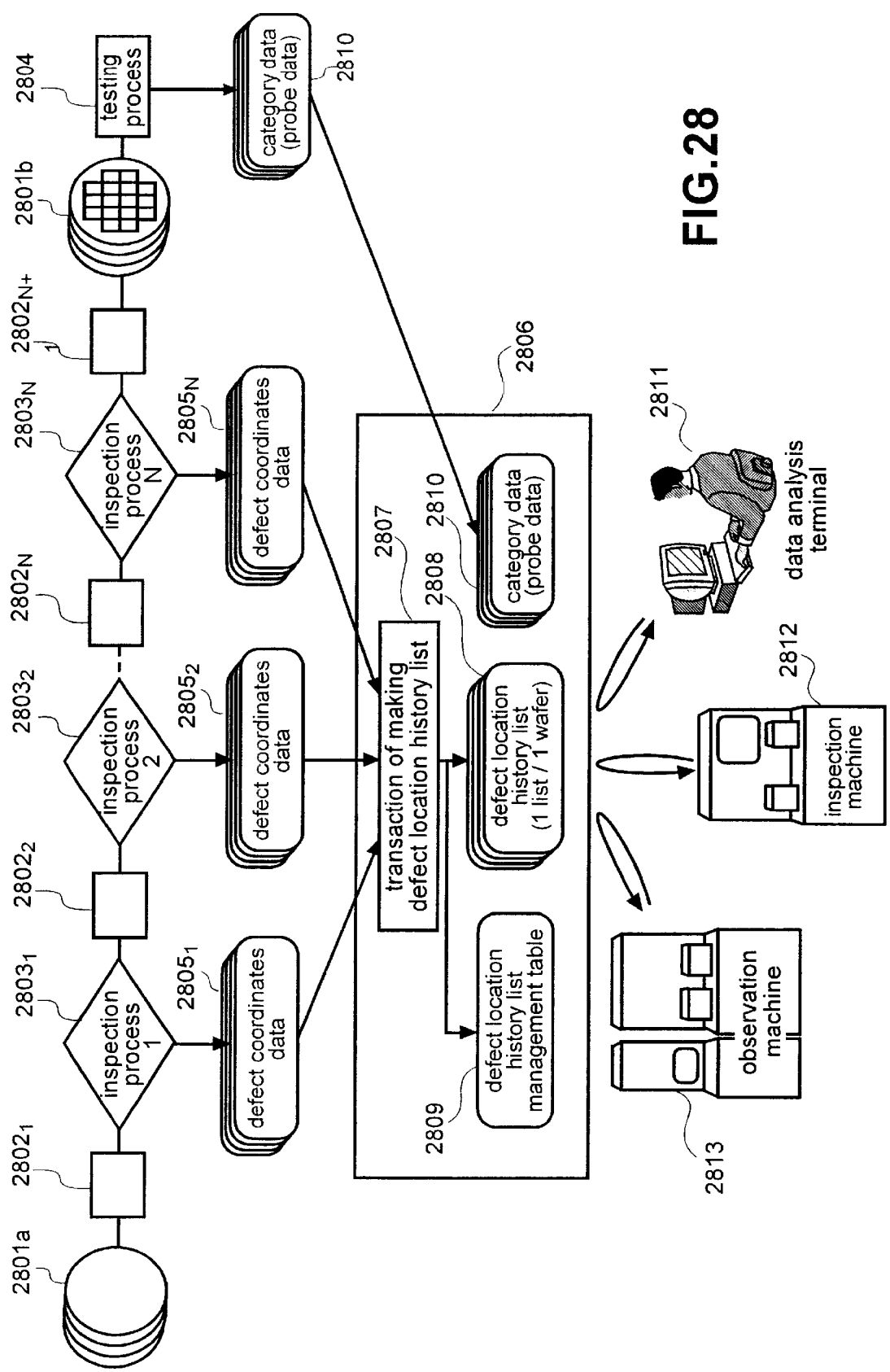
FIG. 28 is a block diagram indicating an example of a system of the present invention for inspecting electronic devices and a method for manufacturing electronic devices using such an electronic device inspecting system.

FIG. 28 is a block diagram indicating an example of a system for inspecting electronic devices and a method for manufacturing electronic devices using such an electronic device inspection system of the present invention. 2801a is a bare wafer and 2801b is a product wafer. 28021, 28022, . . . , 2802N, 2802N+1 are manufacturing processes, 28031, 28032, . . . , 2803N are inspection processes, 2804 is a testing process, 28051, 28052, . . . , 2805N are inspection results, 2806 is an analysis unit, 2807 is a transaction of making a defect location history list, 2808 is a defect location history list, 2809 is a defect location history list management table, 2810 is category data(probe data), 2811 is a data analysis terminal, and 2812 is an inspection machine, and 2813 is an observation machine.

In FIG. 28, the bare wafer 2801a is treated sequentially in the manufacturing processes 28021, 28022, . . . , 2802N, 2802N+1 (when none of those manufacturing processes is specified, it is referred to just as the manufacturing process 2802) for deposition, lithography, etching, etc. In addition, an ion implantation is applied to the bare wafer as needed before the wafer becomes a product wafer 2801b. In each of the manufacturing processes 28021, 28022, . . . , 2802N, 2802N+1 (each consists of a plurality of sub-processes sometimes) is included one of various defect inspection processes such as a particle inspection process and a visual inspection process, as needed. The wafer 2801 treated in those manufacturing processes is then transferred to those defect inspection processes sequentially. In this example, it is premised that each of the inspection processes 28031, 28032, . . . , 2803N (thereunder, these inspection processes will be referred to just as inspection processes 1, 2, . . . , N) is included in each of the manufacturing processes 28021, 28022, . . . , 2802N and those inspection processes are connected to the analysis unit 2806 through a network. Coordinate data of a defect, etc., which are inspection results 28051, 28052, . . . , 2805N of the inspection processes 1, 2, . . . , N (when none of these inspection results is specified, it is referred to as the inspection result 2805) are transmitted to the analysis unit 2806.

The product wafer 2801b obtained through those treatments is then determined for fail or pass of each chip in the testing process 2804. The category data indicating the determination result is also transmitted to the analysis unit 2806 through a network.

In the analysis unit 2806, the transaction of making defect history list 2807 collects inspection results 28051, 28052, . . . , 2805N from the inspection processes 1, 2, . . . , N and processes them in order of process thereby to create a defect location history list 2808 for each wafer. The process 2807 also creates a defect location history list management table 2809 for managing the defect location history list 2808 for each wafer 2801. The list and table are held in the analysis unit 2806. The analysis unit 2806 also holds the category data 2810 obtained in the testing process 2804.

This analysis unit 2806 is also connected to the data analysis terminal 2811, the inspection machine 2812, and the observation machine 2813 through a network. The data analysis terminal 2811 analyzes inspection results using the defect location history list 2808 created in the analysis unit 2806. The inspection machine 2812 inspects defects using the defect location history list 2808 created in the analysis unit 2806. The observation machine 2813 obtains defect images using the defect location history list generated in the analysis unit 2806.

In this embodiment, the inspection machine 2812 executes inspection processes 2801, 2802, . . . , N as needed and transmits defect inspection results to the analysis unit 2806 as inspection results 28051, 28052, . . . , 2805N, and obtains the defect location history list 2808 from the analysis unit 2806 thereby to evaluate the inspection through processing of the defect inspection results using the list. The observation machine 2813 selects each defect properly using the defect inspection results obtained in the inspection machine 2812 and the defect location history list 2808 created in the analysis unit 2806, then takes and stores a photograph of the selected defect image. The data analysis terminal 2811 also analyzes how each manufacturing process causes defects, and searches defects that will cause a defective wafer using the defect location history list 2808, the defect location history list management table 2809, and the category data 2810 from the analysis unit 2806.

FIG. 29 shows an example of a defect location history list 2808 shown in FIG. 28.

The defect location history list 2808 describes the history of defects generated on a wafer in the production line shown in FIG. 28. Consequently, one defect location history list 2808 is created for one wafer 2801.

In FIG. 29, this defect location history list describes the items of identification information (2901–2903) of the object wafer, a transaction parameter of making defect location history list 2904, and the inspection process name 2905 in the head portion. In this example, the wafer identification information has product name 2901, lot number 2902, and wafer number 2903 of the wafer. The transaction parameter of making defect location history list 2904 is used for the transaction of cluster identification and for the transaction of process identification, which are described later. The inspection process name 2905 describes the names of the manufacturing processes which are arranged in the order in which the wafer is inspected. In this example, the wafer is inspected in each of the inspection processes 1, 2, and 3 following each of the manufacturing processes 1, 2, and 3 shown in FIG. 28. Consequently, inspection processes 1, 2, and 3 are described here as the inspection process name 2905.

Then, on the left side in this defect location history list shown in FIG. 29 is provided a "defect coordinates" item 2906. In this item are described the coordinates of every defect detected on the wafer in the three inspection processes 1, 2, and 3 (sequential numbers of the defects are given in parenthesis for convenience sake.). However, considering the coordinate detecting accuracy of the object inspection machine, the coordinates of each defect detected in subsequent processes, for example, within a fine radius range referred to as the comparative radius of a defect detected earlier are assumed to be the same as the coordinates of the early-detected defect. In other words, although an inspection process detects defects one by one and transmits the defects to the analysis unit 2806 sequentially in FIG. 28, the transaction of making defect history list 2807 processes an inspection result 2805 each time it receives an inspection result and adds the result to the defect location history list 2808. In FIG. 29, the "defect coordinates" in this example mean coordinates in an x, y coordinate system. The left part in the "defect coordinates" 2906 indicates an x coordinate (distance unit=($\mu$m) and the right part indicates a y coordinate (distance unit=($\mu$m). The coordinates (x, y) of the first detected defect thus becomes (23115.70, 45894.32).

A "defect count in each process" item 2907 comes after the "defect coordinates" 2906. The item 2907 indicates how many defects are detected in a defect category in each of the inspection processes 1, 2, and 3 described for the "inspection process name" item 2905. Inspection processes 1, 2, and 3 are described in order from the left side. "0" means that no defect is detected, "1" means that one defect is detected, and "2" means that two defects are detected.

For example, at the first described coordinates (23115.70, 45894.32), one defect is detected in the inspection processes 1 and 3 respectively and no defect is detected in the inspection process 2. At the fourth described coordinates (10778.87, 6274.35), one defect is detected in the inspection processes 1 and 2, but two defects are detected in the inspection process 3. And, at the sixth described coordinates (−18781.02, 290487.29), one defect is detected in the inspection process 1 and none in other inspection processes. At the eleventh described coordinates (−917.65, −2617.23), one defect is detected only in the inspection process 2. And at the seventeenth described coordinates (6938.41, 941.94), one defect is detected only in the inspection process 3. In such a way, some defects are detected only in a single inspection process. Just like the first described defect, however, some defects are detected in the first inspection process, but not detected in the next inspection process 2, and detected again in the next inspection process 3. This "defect count in each process" item 2907 provides such information of defects.

Detection of two defects described above means detection of two defects at the same coordinates. In this case, it means that two defects positioned very closely to each other are regarded to be at one coordinate position and other defects detected within a fine radius range in the proximity of an already detected defect, which is referred to as a comparative radius, are assumed to be the defects positioned at the same coordinates as those of the first-detected one. This comparative radius is set beforehand as a processing parameter corresponding to an object detecting sensibility. For example, it is set to about 250 $\mu$m.

Following the "defect count in each process" item 2907 comes a "defect generated process" item 2908. This item 2908 indicates the first inspection process in which an object defect is detected. The inspection process is indicated with an 8-bit decimal number for easier understanding. "0" means the inspection process 1, "1" means the inspection process 2, and "2" means the inspection process 3 in which an object defect is detected for the first time respectively. The maximum 8-bit value ("225" as a decimal number) indicates that no defect is detected. Also in this case, the inspection processes 1, 2, and 3 are described in order from the left side.

Consequently, for example, although the first or fourth described defect is detected in the inspection process 3, it will be understood that the defect is detected for the first time in the inspection process 1, since "0" is described for the defect. For the sixteenth described defect detected at the coordinates (−27068.01, −7597.72) in the inspection process 3, "1" is described for the defect. It will thus be understood that the defect is detected for the first time in the inspection process 2. By referencing to the defect generated process in this way, it is possible to easily determine the first inspection process in which an object defect is detected.

Following the "defect generated process" item 2908 comes a "defect size" item 2909. This item 2909 indicates the size of each detected defect and the size is classified by class and represented by a number like 1, 2, 3. The larger the number is, the larger the defect is.

Following the "defect size" item 2909 comes a "defect category" item 2910. This item 2910 indicates a result of classification performed by predetermined category. In this example, 1 to 9 are used as defect classification numbers.

Following the "defect category" item 2910 comes a "cluster" item 2911. This item 2911 indicates a result of a determination of the density of defect coordinates.

A density of defect coordinates is determined as follows, for example. At first, the top area of a wafer is divided into two-dimensional fine rectangular areas and each of those rectangular areas is substituted for an image assuming that "1" is assigned for each rectangular area in which a defect is found and "0" is assigned for each rectangular area in which no defect is found. Then, each image is expanded to determine whether or not adjacent rectangular areas are connected to each other (for example, rectangular areas of adjacent images 1 are determined to be connected), and if the number of defects in a group of rectangular areas connected to each other (connected areas) exceeds a threshold value, the density is determined to be high. A group of defects whose density is determined to be high is referred to as a cluster of defects.

In the "cluster" item 2911, a unique ID number is given to each cluster defect and the ID number is described for the coordinates of each defect. In this example, the fifth, sixth, and seventh defects detected in the inspection process 1 are cluster defects and an ID number "1" is given to those cluster defects respectively. If there are other cluster defects, "2" is given to them. In the inspection process 2, the twelfth and thirteenth defects are determined to be cluster defects.

An "image index" item 2912 comes after the "cluster" item 2911. This "image index" item 2912 indicates an index (number) of an image which is already photographed. Image indexes are assigned for each inspection process. In this example, capturing an image means photographing and storing an image of a defect detected on a wafer 2801 in the observation machine 2813 shown in FIG. 28. The above index, therefore, means a number for a stored defect image, as well.

In this example, images are captured sequentially from the fourth, fifth, and tenth defects according to the inspection results obtained in the inspection process 1. Then, according to the inspection results obtained in the inspection process 2, images are captured from the fourth, twelfth, and fourteenth defects in order. After this, according to the inspection results obtained in the inspection process 3, images are captured sequentially from the fourth, eighth, and seventeenth defects. The image of the fourth defect is captured in each of the inspection processes 1, 2, and 3. Defects whose images are captured in such a way are, for example, determined to be large in size in the "defect size" item 2909. In addition, of the defects detected in the inspection process 1, watched defects (because of the size and position) can be set so that their images are captured in each inspection process just like, the fourth defect described above.

Figure 30:
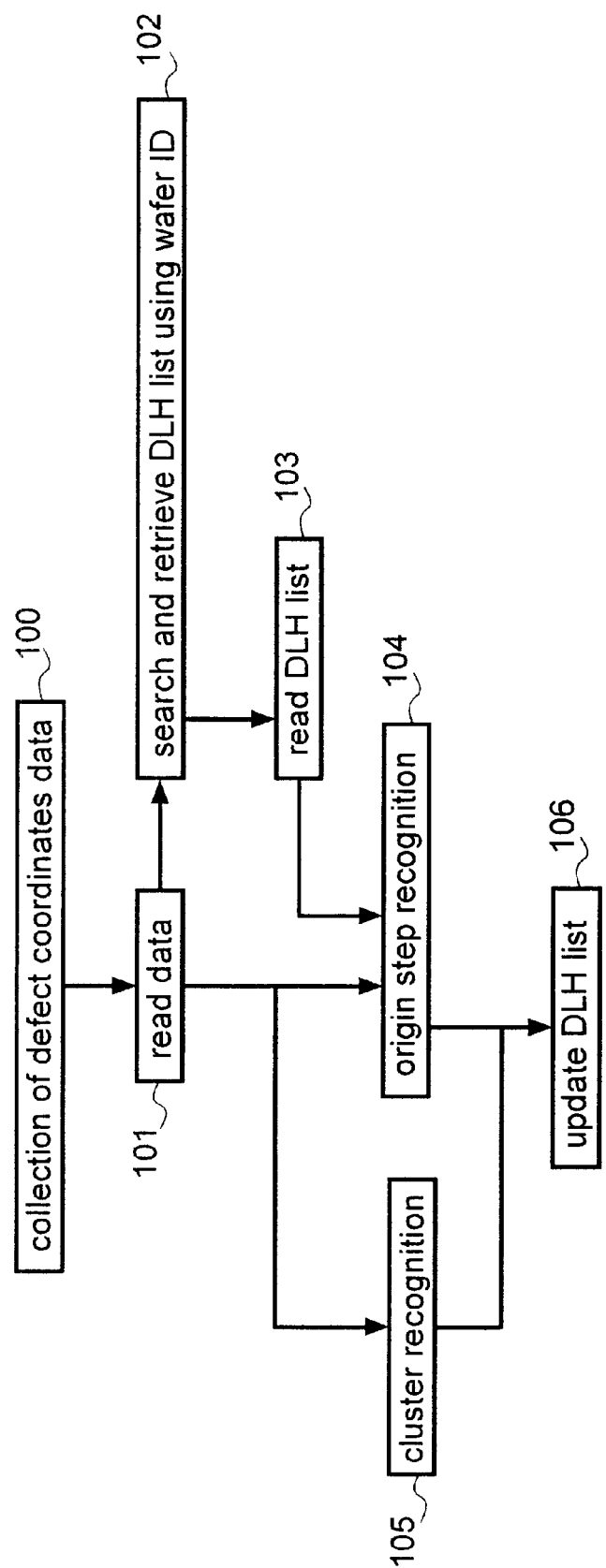
FIG. 30 is a flow chart indicating a concrete example of a defect location history list creating operation of the analysis unit shown in FIG. 28.

FIG. 30 is a flow chart indicating an example of a transaction of making defect location history list 2807 in the analysis unit 2806 shown in FIG. 28.

In FIG. 30, receiving an inspection result 2805 from the inspection process 2803 (step 100), the analysis unit 2806 reads the result 2805 and goes into the transaction of making defect history list 2807 (step 101). In this process, the analysis unit 2806 searches and obtains a defect location history list 2808 created already for the object wafer 2801 (step 102) and reads the list 2808 (step 103).

Then, the analysis unit 2806 determines whether or not the coordinates of the defect corresponding to the read inspection result(defect coordinates data) 2805 is registered in this read defect location history list 2808 thereby to check if the defect is a new one or a past one detected in this inspection process 2803 (step 104). In addition, the analysis unit 2806 identifies the cluster of the defect from the inspection result 2805 (step 105). Then, according to the size information of the defect obtained from this processing and the inspection result 2805, the analysis unit 2806 updates the defect location history list 2808 with this new inspection result 2805 (step 106).

Thus, FIG. 29 shows the defect location history list 2808 in which the inspection results obtained from the inspection processes 1, 2, and 3 shown in FIG. 28 are registered. However, when receiving the inspection result 28054 from the next inspection process 4 (inspection process 28034), the analysis unit 2806 provides the defect location history list 2808 with fields of this inspection process 4, each item in those fields corresponding to each of the items such as "defect count in each process", "defect generated process", "defect size", "defect category", "cluster", and "image index". Then, the analysis unit 2806 describes predetermined data in the item fields of the inspection process 4 corresponding to "defect count in each process", etc., regarding all the defects positioned within the comparative radius range of the coordinates of the defect registered already in this inspection result 28054 as the same defects as the already-registered defect. In addition, other defects positioned at coordinates other than those of the defect registered already in this inspection result 28054 are regarded as new defects detected in this inspection process 4 and the coordinates of the defect are added in the "defect coordinates" item 2906. Also, predetermined data for such defects is described in the item fields of the inspection process 4 corresponding to each of the above items for registration.

Going through the inspection processes 5, 6, etc. in this way, the inspection results 2805 of those processes are registered sequentially in the defect location history list.

Next, a description will be made of the processing time and the evaluation result of file volume for creating a defect location history list 2808.

Figure 31:
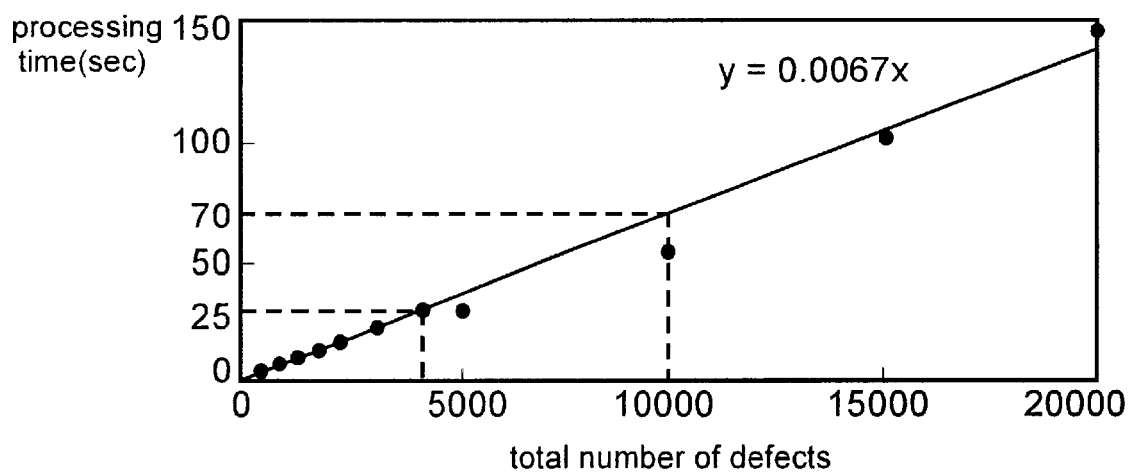
FIG. 31 shows a test example of the defect location history list processing time shown in FIG. 29 with respect to the total number of defects.

FIG. 31 shows a test result of the processing time of the defect location history list 2808 with respect to the total number of defects on a wafer. A Sun SPARC station 10 (32 MB memory) was used for this evaluation.

In FIG. 31, when 20 processes were inspected at a rate of 200 defects/inspection process, the total number of defects was 4000. The processing time of a defect location history list 8 was thus estimated to be about 25 seconds. If the total number of defects exceeds 10,000 in an visual inspection, a defect location history list 8 is created in about 70 seconds.

Figure 32:
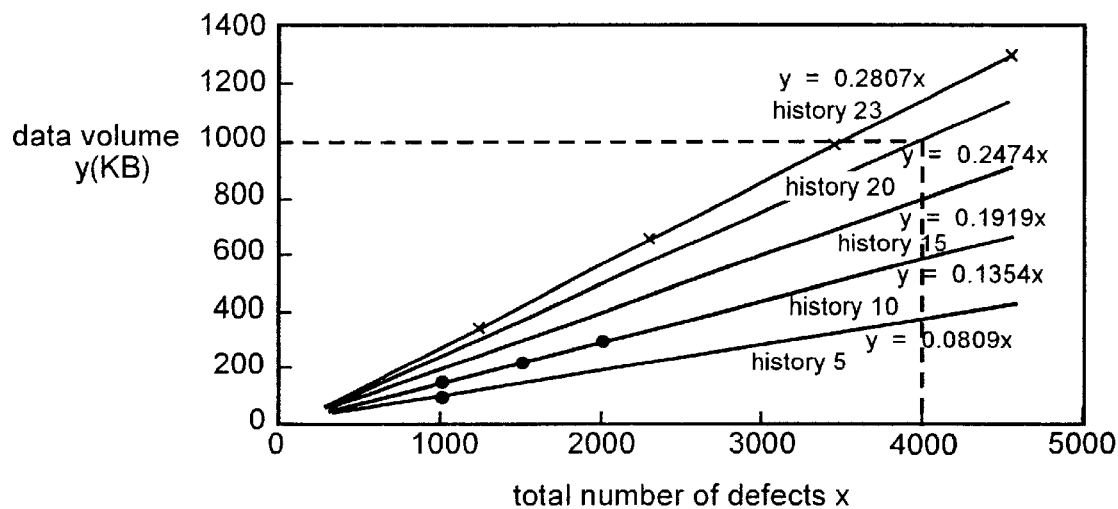
FIG. 32 shows a test example of a data volume of the defect location history list shown in FIG. 29 with respect to the total number of defects.

FIG. 32 shows a test result of a file (data) capacity of a defect location history list 2808 with respect to the total number of defects on a wafer.

In FIG. 32, the functions of the file volume were set as follows with respect to the total number of defects in a defect location history list 2808 created according to the data of inspection carried out i times; the function x is assumed as the total number of defects and the function y of the defect history i is indicated as (a×x). For example, the file volume for the total number of defects in the defect location history list created with inspection data of 20 times is represented as function y of defect history 20=0.2474x. Consequently, the file volume is estimated to be about 1 MB if 20 processes are inspected at a rate of 200 defects/inspection process.

Figure 33:
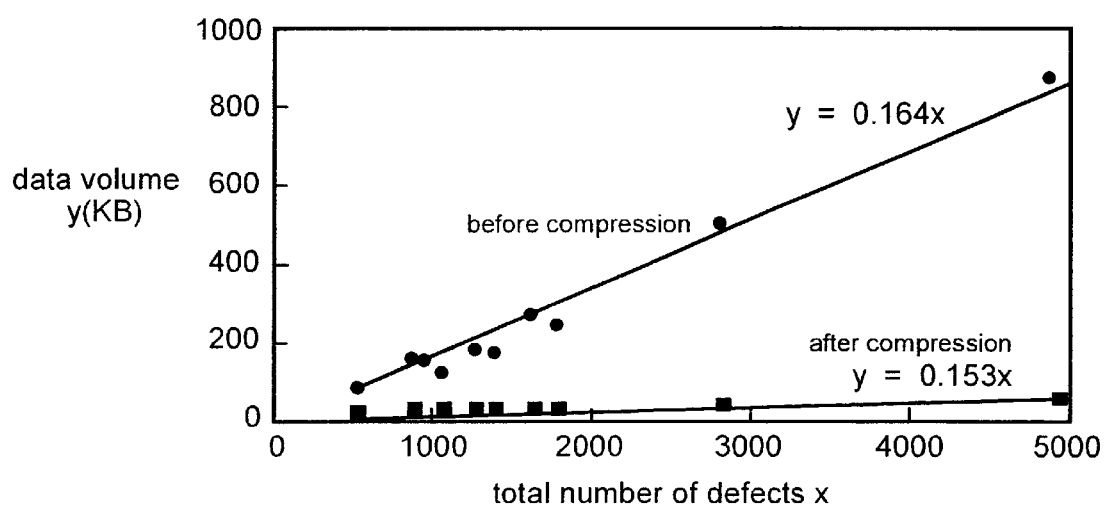
FIG. 33 shows a test example of a compressed data amount of the defect location history list shown in FIG. 29 with respect to the total number of defects.

FIG. 33 shows a test result of the file compression effect when the file of a defect location history list 2808 is compressed using a data compression technology.

In FIG. 33, a file can be compressed to about 1/10 in capacity using the UNIX compress command. If it is assumed that the function of the normal file volume is y=0.164x with respect to the total number of defects in a defect location history list 2808, the file volume can be compressed up to about 1/10, that is, y=0.0153x. According to this result, if 50 wafers are produced per day and a 1 MB defect location history list 2808 is created from inspection data of 20 inspection processes per wafer, it is possible to store only the defect location history lists 2808 for 40 days (i.e., 2000 MB÷(50 wafers/day×1 MB/wafer) using a 2 GB hard disk. If the above file compression method is used, however, it is possible to store defect location history lists for 400 days, that is, over one year, which is ten times the initial one with no problems in practical use.

Figure 34:
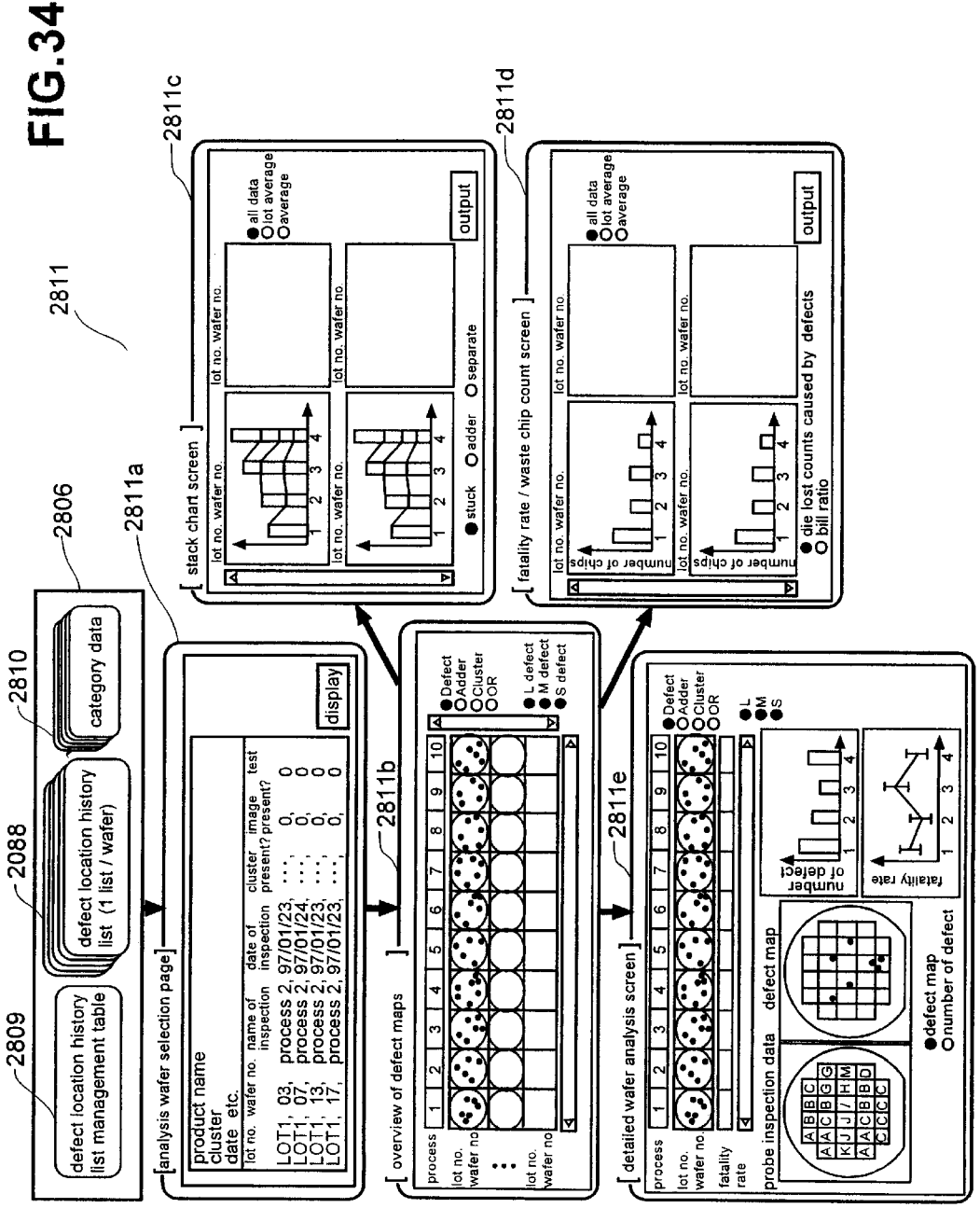
FIG. 34 shows the operation functions of the data analysis terminal shown in FIG. 28.

FIG. 34 shows an example of an analyzing operation of the data analysis terminal 2811 shown in FIG. 28 using a defect location history list 2808. In FIG. 28, the same numerals are used for the same items as those shown in FIG. 28, avoiding redundant description.

In FIG. 34, when an inspection result is analyzed in the data analysis terminal 2811, the data analysis terminal 2811 reads the defect location history list 2808, the defect location history list management table 2809 for managing the defect location history list 2808, and the category data 2810, which is probe testing data, from the analysis unit 2806 respectively. The defect location history list management table 2809 describes the identifiers of each wafer, for example, type, lot, process name, the number of inspected processes, and outline of each inspection result (inspection process name, foreign particle/visual inspection identifier, image presence/absence flag, inspection date, cluster presence/absence flag, etc.). The category data 2810 indicates the electrical inspection result of each chip of a product wafer 2801b (FIG. 28). This category data 2810 enables determination of fail/pass for each chip on a wafer 2801b.

After those data items are read, the analysis wafer selection page 2811a is displayed. On this analysis wafer selection page 2811a, it is possible to select a plurality of object wafers (to be analyzed) according to the information of the defect location history list management table 2809.

If a desired wafer is selected for analysis on the analysis wafer selection page 2811a, the overview of defect map 2811b is displayed. On this screen 2811b, it is possible to check how defects are distributed on each of selected wafers in each inspection process. This defect distribution state in each inspection process is displayed with the coordinates (x, y) registered for the "defect coordinates" item 2906 (FIG. 29) in the object defect location history list 2808.

In this case, both display data and display conditions can be selected. In this example, display data is set to "Defect" and defects detected in each inspection process are displayed using the coordinates set in the "defect coordinates" item 2906 and the data set in the "defect count in each process" item 2907 in the defect location history list 2808. If "L", "M", and "S" are selected as display conditions, defects in all sizes are displayed. If "Added" is selected as display data, the defects to be displayed are only those selected using the data set in the "defect generated process" item 2908 from those positioned at the coordinates set in the "defect coordinates" item 2906 in the defect location history list 2808 and detected newly in each inspection process. If "cluster" is selected, the defects to be displayed are only the cluster defects selected using the data set in the "cluster" item 2910 from those positioned at the coordinates set in the "defect coordinates" item 2906 in the defect location history list 2808 and detected in each inspection process. If "OR" is selected, the defects to be displayed are all those detected so far in all the inspection processes including the current one (for example, when the current inspection process is i, all the defects detected in the inspection processes 1 to i are displayed) when the data set in the "defect generated process" item 2908 is added to the coordinates set in the "defect coordinates" item 2906 in the defect location history list 2808. In addition, if any one of the display conditions "L", "M", and "S" is selected, it is possible to display the distribution of defects in each size by using the coordinates set in the "defect coordinates" item 2905 and the data set in the "defect size" item 2909 in the defect location history list 2808.

If the data analysis terminal 2811 is operated as predetermined when the overview of defect map 2811b is displayed, a vertical bar graph (stack chart) obtained by classifying the number of detected defects in each process by the defect generated process can be displayed for each of the selected wafers (stack chart screen 2811c). This stack chart is obtained by adding the data set in the "defect generated process" item 2908 in the defect location history list 2808 for each defect generated process. A display unit can also be selected from all data (for each wafer), lot average, and total average.

If the data analysis terminal 2811 is operated as predetermined when the overview of defect map 2811b is displayed, it is possible to display the number of chips (lost chip count) that would be defective due to a defect newly detected on each of the selected wafers in each manufacturing process using the category data 2810 read from the analysis unit 2806 (kill ratio/lost chip count screen 2811d).

If a desired wafer is specified using the cursor and the SELECT button is pressed on the displayed overview of defect map 2811b, the detailed wafer analysis screen 2811e is displayed for the specified wafer.

This detailed wafer analysis screen 2811e displays how the defects are distributed on this specified wafer in each inspection process, as well as the probe testing data indicating ranks A, B, C, etc. for fail/pass of each chip in performance obtained according to the category data 2810, a defect map indicating how defects detected in a specified inspection process are distributed, a graph indicating the number of defects detected newly in an inspection process, and a possibility (kill ratio) of causing a defective chip due to the defects detected newly in each inspection process. (In this kill ratio graph, the higher the kill ratio is in an inspection process, the more easily defective chips are generated. The illustrated graph indicates that defective chips are easily generated in the inspection process 3 of the manufacturing process 28033 (FIG. 28).)

As described above, the data analysis terminal 2811 can analyze and evaluate instantly how defects are generated on a desired wafer in a predetermined process, as well as each process in which defects are caused using the defect location history list 2808 and the category data 2810.

Figure 35:
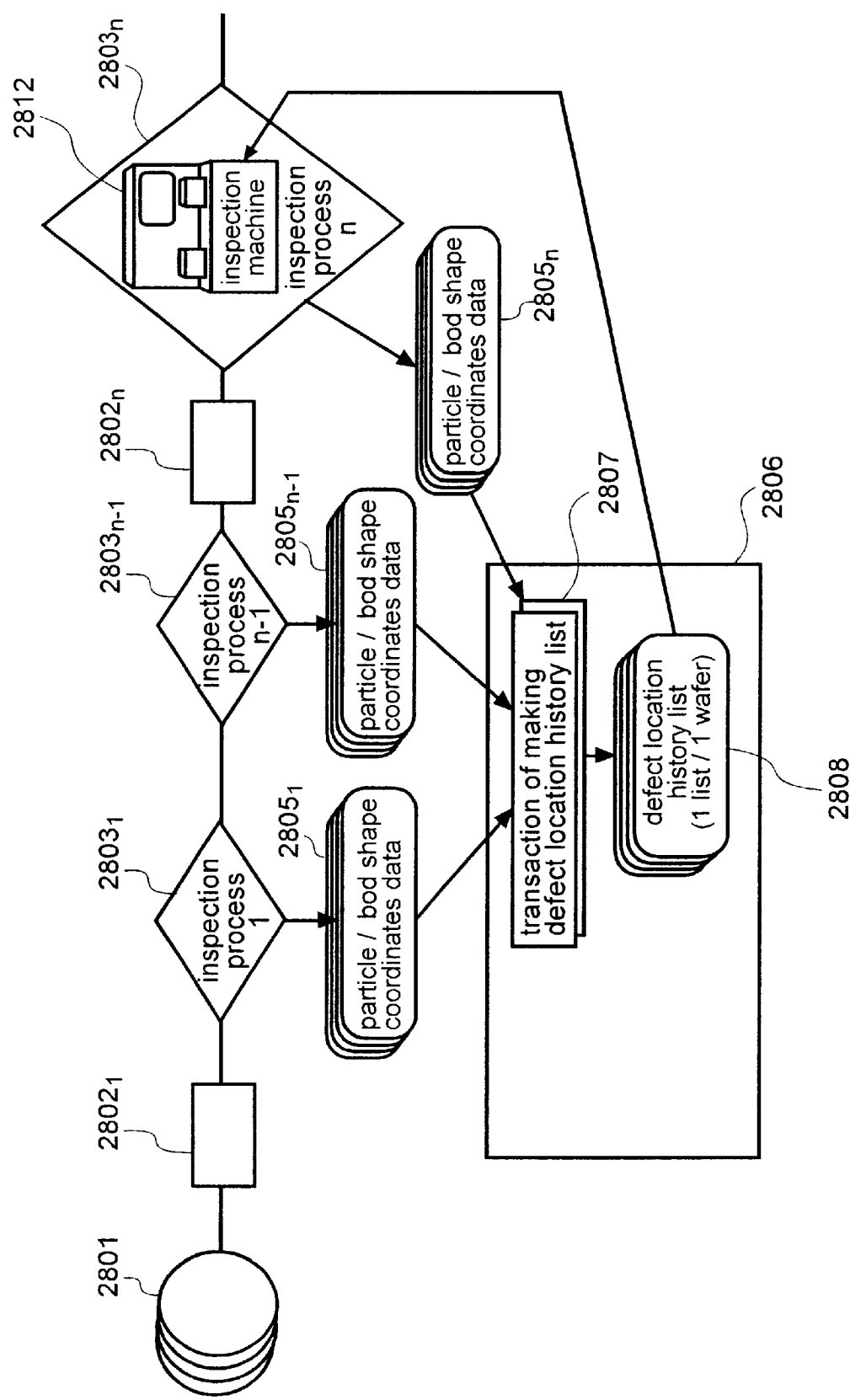
FIG. 35 shows the functions of the inspection machine shown in FIG. 28.

FIG. 35 is a block diagram of the inspection machine 2812 shown in FIG. 28. In FIG. 35, the same numerals are used for the same items as those in FIG. 28, avoiding redundant description.

The inspection machine 2812 is composed so as to execute inspection processes of wafers and transmit obtained inspection results to the analysis unit 2806, as well as process the inspection results thereby to distinguish defects. In FIG. 35, the inspection machine 2812 executes the n-th (n=1, 2, . . . , N) inspection process n. This inspection machine 2812 supplies the inspection result 2805n obtained for a wafer treated in the manufacturing process 2802n to the analysis unit 2806 as described above and obtains the defect location history list 2808 of this wafer created on the basis of the inspection results 28051 to 2805n-1 of the inspection processes 1 to n-1 from the analysis unit 2806 using the identifiers of the wafer, such as type, lot, and wafer number. Then, the inspection machine 2812 processes the inspection result 2805n using the defect location history list 2808, thereby to select a desired defect and obtain the information thereof.

Figure 36:
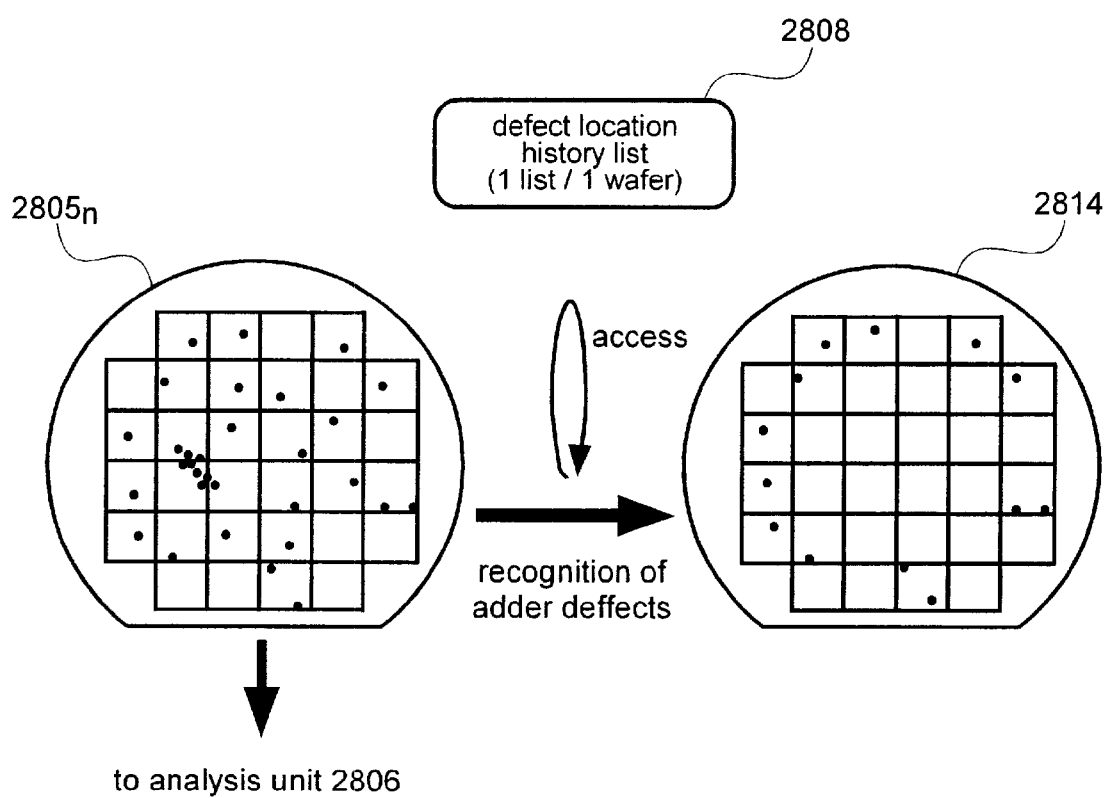
FIG. 36 shows an operation of the inspection machine shown in FIG. 35.

For example, as shown in FIG. 36, of the inspection results 2805n obtained by the inspection machine 2812, the coordinates (set in the "defect coordinates" item 2906 in FIG. 28) of a defect registered already in a defect location history list 2808 are referenced thereby to remove the defects detected in the inspection processes 1 to n-1. And accordingly, defects detected newly in the inspection process n are selected and the information 2814 is obtained. The information 2814 is then displayed on a screen so that the distribution of the defects on an object wafer, as well as a tendency with which defects are generated in the manufacturing process 2802n (FIG. 35) can be found (in FIG. 36, defects are apt to occur in the peripheral portion of a wafer). Thus, proper measures can be taken to prevent those defects.

Figure 37:
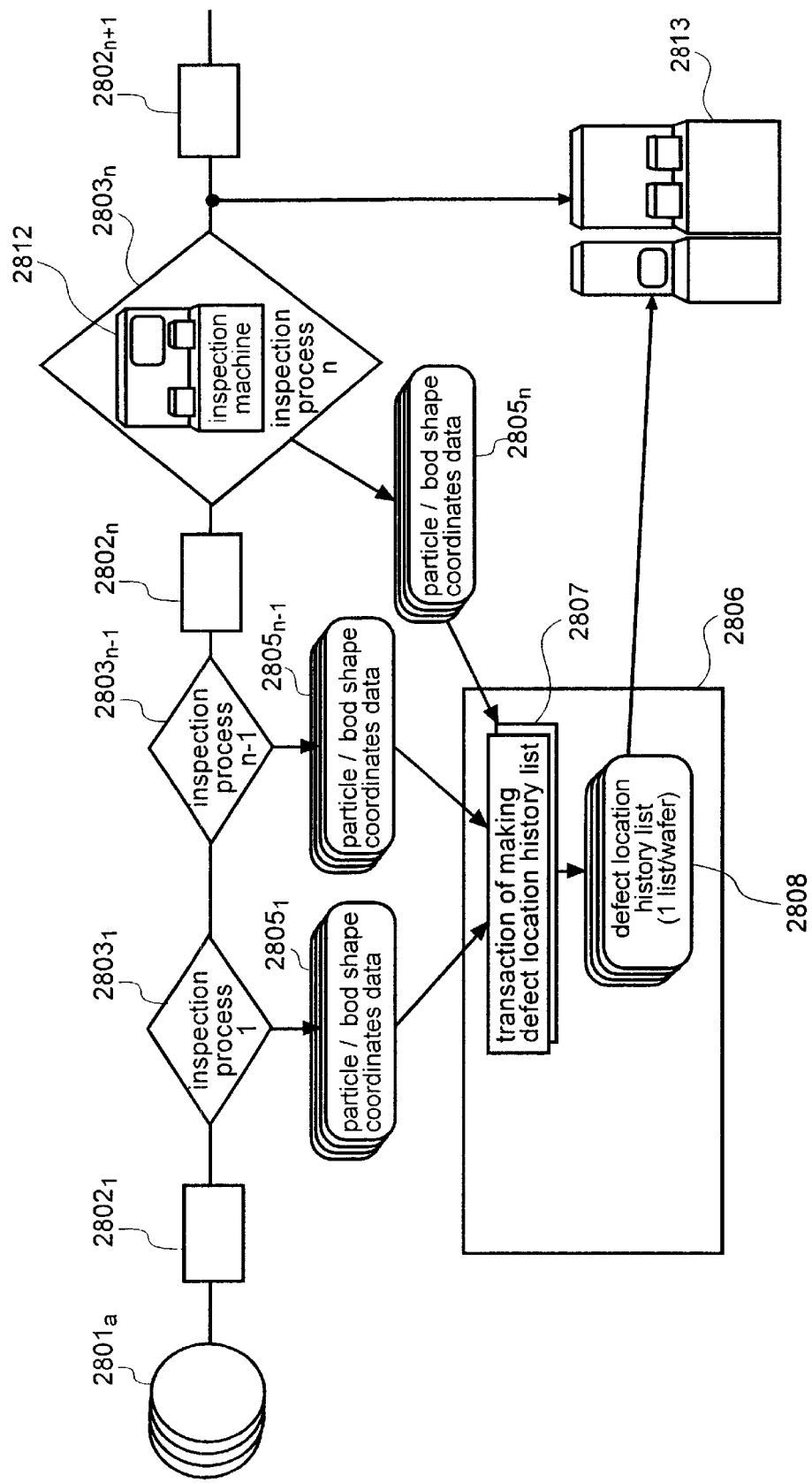
FIG. 37 shows the operation functions of the observation machine shown in FIG. 28.

FIG. 37 is a block diagram of the observation machine 2813 shown in FIG. 28. The same numerals are used for the same items as those shown in FIG. 28, avoiding redundant description.

In FIG. 37, the observation machine 2813 photographs a desired detected defect image using a still camera or a video camera and stores the image on film or on a recording medium (storing a defect image in this way is referred to as image capturing). The observation machine 2813 selects a desired one of the defects detected by the inspection machine 2812 to obtain a desired defect image therefrom.

Figure 38:
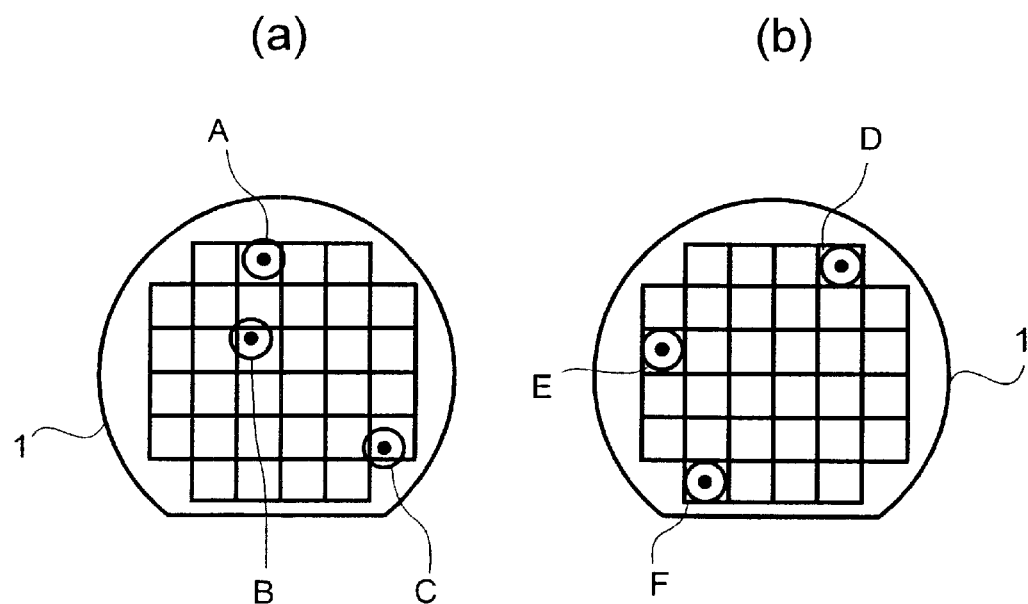
FIG. 38 shows an operation of the observation machine shown in FIG. 37.

FIG. 38(a) shows a concrete example of the distribution of the newly detected defects on a wafer 2801 in the inspection process n shown in FIG. 37. In this example, there are three new defects, which are assumed as A, B, and C. Such a selection of the defects is made by referencing to the defect location history list 2808 of the wafer 2801 created using the inspection result 2805n obtained in the inspection process n. The observation machine 2813 displays an image as shown in FIG. 38(a). The user can select any defect whose image is needed from the defects A, B, and C.

FIG. 38(b) indicates the distribution of the defects D, E, and F selected from those detected in the inspection process n. The defects D to F are those detected already in any of the inspection processes 1 to n-1, then photographed and stored.

For this selection in the observation machine 2813, the registered data in "defect coordinates" item 2906 and "image index" item 2912 (FIG. 29) in the defect location history list of the wafer 2801 are used. Also in this case, an image as shown in FIG. 38(b) is displayed and the user can select any of the defects D, E, and F so as to capture the image.

As for each defect photographed and stored in the observation machine 2813, the analysis unit 2806 sets a specific index for the defect and this index is registered in this defect field of the "image index" item 2911 (FIG. 29) in the defect location history list 2808 updated according to the inspection result 2805n of the inspection process n. In other words, this index is registered in a field decided uniquely by the coordinates and the inspection process name of the defect. In addition, this index is given to a film, etc. used for recording and storing the image of this defect.

Figure 39:
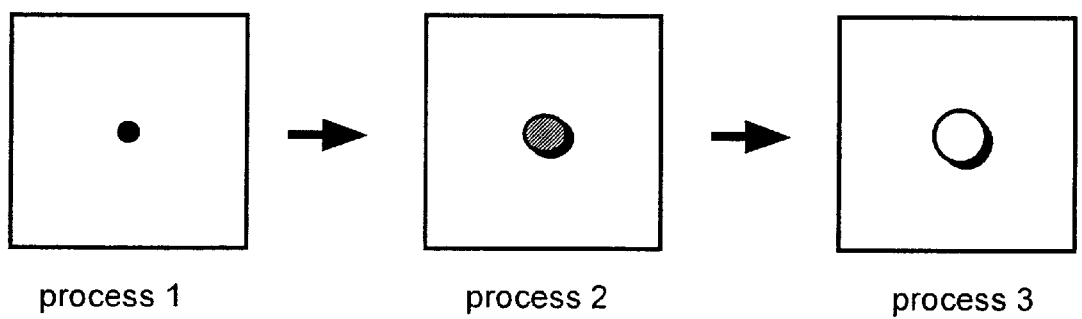
FIG. 39 shows an example for how to use an image captured in the observation machine shown in FIG. 28.

Consequently, the data analysis terminal 2811 can observe the image of the defect using the stored film in this way, as well as observe the progress and changes of the same defect sequentially in manufacturing processes, for example, in those as shown in FIG. 39. Such a film that records the defect can be identified easily from the registered data in the "defect coordinates" item 2906 and the "image index" item 2912 (FIG. 29) in the defect location history list 2808 of the wafer.

In FIG. 37, the observation machine 2813 references to a defect location history list 2808 created beforehand thereby to select an object defect to be photographed and stored, but the observation machine 2813 may also select the object defect by itself as shown in FIGS. 38(a) and (b). In such a case, the observation machine 2813 in FIG. 37 reads the inspection result 2805n from the inspection machine 2812 and the defect location history list 2808 for up to the inspection result 2805 from the analysis unit 2806, then select an object defect as shown in FIGS. 38(a) and (b) from the defects in the inspection result 2805n using the data registered in this defect location history list 2808.

As described above, a defect location history list includes all the past information related to each defect on a wafer 2801 in this example, so it is possible to obtain useful defect image data that indicates the defect origin clearly.

Although the above example focuses on a method for manufacturing semiconductor devices, the present invention is not limited only to that; it can also apply to any production lines of products (e.g., magnetic disks, circuit boards, etc.) that require work defect inspections and product functional tests, of course.

The inspection history list may also include results of analysis and/or measurement performed by an elemental analyzer and a film thickness measuring machine.

As described above, according to the present invention, a mass of defect data can be pigeonholed so as to be stored as defect location history lists for easier use. It is thus possible to reduce the preparing time for analysis thereby to reduce the analyzing time and improve the analyzing accuracy.

We claim:

1. An inspection system comprising:
   an inspection machine for inspecting a work which is processed in a manufacturing process and providing an inspected result; and
   an analysis system for outputting an inspection history list obtained by making calculations from the inspected result, said inspection history list showing a matrix of first information as to inspection processes in which the work is inspected or manufacturing processes corresponding to the inspection processes in which the work is inspected and second information as to the work inspected by the inspection machine.

2. The inspection system according to claim 1, wherein the inspection history list shows whether or not characteristic defects are included in the inspection result of the inspection process in which the work is inspected or the manufacturing process corresponding to the inspection process in which the work is inspected.

3. The inspection system according to claim 2, wherein the characteristic defect is a cluster.

4. The inspection system according to claim 1, wherein the inspection system further includes a test machine for testing an electrical characteristic of the work and the inspection history list shows whether or not the electrical characteristic of the work is included.

5. The inspection system according to claim 1, wherein the inspection system further includes a plurality of the inspection machines, and wherein the inspection machines include at least one visual inspection machine and a particle inspection machine.

6. The inspection system according to claim 1, wherein the inspection system further includes an observation machine for capturing a defect image of the work and the inspection history list shows whether or not the defect image of the work is included in the inspection result of the inspection process in which the work is inspected or the manufacturing process corresponding to the inspection process in which the work is inspected.

7. The inspection system according to claim 1, wherein the analysis system comprises a client-server system.

8. The inspection system according to claim 1, wherein the first information further includes the inspection processes in which a work is not inspected or the manufacturing processes corresponding to the inspection processes in which a work is not inspected.

9. The inspection system according to claim 1, wherein a plurality of said works are inspected and wherein the analysis system creates a defect location history list for each of said works according to inspection results obtained by the inspection machine before receiving an analysis instruction.

10. The inspection system according to claim 9, wherein the analysis system creates the inspection history list by using the defect location history list.

11. An inspection system comprising:
    an inspection machine for inspecting a work which is processed in a manufacturing process; and
    an analysis system for displaying a matrix of first information as to inspection processes in which the work is inspected or manufacturing processes corresponding to the inspection processes in which the work is inspected and second information as to the work inspected by the inspected machine.

12. An inspection system comprising:
    an inspection machine for inspecting a work which is processed in a manufacturing process; and
    an analysis system for displaying both inspection processes in which the work is inspected and inspection processes in which the work is not inspected or both manufacturing processes corresponding to the inspection processes in which the work is inspected and manufacturing processes corresponding to the inspection processes in which the work is not inspected.

13. An analysis system comprising:
    storing means for storing inspection results of an inspected work; and outputting means for outputting an inspection history list calculated by using said stored inspection results, said inspection history list showing a matrix of first information as to inspection processes in which the work is inspected or manufacturing processes corresponding to the inspection processes in which the work is inspected and second information as to the work inspected by the inspected machine.

14. The analysis system according to claim 13, wherein the first information further includes the inspection processes in which the work is not inspected or the manufacturing processes corresponding to the inspection processes in which the work is not inspected.

15. A method for producing electrical devices comprising:

a processing step for processing works in a manufacturing line;

a inspecting step for inspecting a work which is processed in one of the manufacturing processes of the manufacturing line by an inspection machine to produce an inspected result;

a analyzing step for analyzing defects information obtained by making calculations from the inspected result, said defects information showing a matrix of first information as to inspection processes in which the work is inspected or manufacturing processes corresponding to the inspection processes in which the work is inspected and second information as to a plurality of the works inspected by the inspected machine; and a controlling step for controlling the manufacturing line on the basis of the result of the analysis.

16. The method according to claim 15, wherein the defects information shows whether or not characteristic defects are included in the inspection result of the inspection process in which the work is inspected or the manufacturing process corresponding to the inspection process in which the work is inspected, said analyzing step analyzing defects information without the characteristic defects.

17. The method according to claim 15, wherein the characteristic defect is a cluster.

* * * * *